US006077691A

United States Patent [19]

Dorner et al.

[11] Patent Number: 6,077,691

[45] **Date of Patent: *Jun. 20, 2000**

[54] HIGH LEVEL EXPRESSION OF POLYPEPTIDE THAT CONTAINS MODIFIED PRES1 REGION OF HEPATITIS B VIRUS LARGE ANTIGEN

[75] Inventors: Friedrich Dorner, Vienna; Michael Pfleiderer, Breitstetten; Falko-Günter Falkner, Mannsdorf, all of Austria

[73] Assignee: Baxter Aktiengesellschaft, Vienna, Austria

[ * ] Notice: This patent issued on a continued prosecution application filed under 37 CFR 1.53(d), and is subject to the twenty year patent term provisions of 35 U.S.C. 154(a)(2).

[21] Appl. No.: 08/796,415

[22] Filed: Feb. 6, 1997

Related U.S. Application Data

[62] Division of application No. 08/440,682, May 15, 1995, which is a continuation of application No. 08/099,351, Jul. 30, 1993, abandoned.

[51] Int. Cl.[7] .......................... C12P 21/00; C12N 15/51; A61K 39/29

[52] U.S. Cl. .................... 435/69.3; 435/69.7; 435/320.1; 424/227.1

[58] Field of Search ................................ 435/69.3, 69.7, 435/320.1; 424/227.1

[56] References Cited

U.S. PATENT DOCUMENTS

| | | | |
|---|---|---|---|
| 4,847,080 | 7/1989 | Neurath et al. | 424/89 |
| 5,077,213 | 12/1991 | Li et al. | 435/235.1 |

OTHER PUBLICATIONS

Cheng et al. "Hepatitis B Virus Large Surface Protein Is Not Secreted But Is Immunogenic When Selectively Expressed . . . ", *J. Virol.*, 60(2): 337–344 (1986).

Cheng et al. "Selective Synthesis and Secretion of Particles Composed of the Hepatitis B Virus Middle Surface Protein . . . ", *J. Virol.*, 61(4): 1286–1290 (1987).

Elroy–Stein et al. "Cap–independent Translation of mRNA Conferred by Encephalomyocarditis Virus 5 Sequence . . . ", *Proc. Natl. Acad. Sci. USA*, 86: 6126–6130 (1989).

Fuerst et al. "Use of a Hybrid Vaccinia Virus–T7 RNA Polymerase System for Expression of Target Genes", *Mol. and Cellular Biol.*, 7(7): 2538–2544 (1987).

Kutinova et al. "A Recombinant Vaccinia Virus Expressing Hepatitis B Virus Middle Surface Protein . . . " *Arch. Virol.*, 112: 181–193 (1990).

Prange et al. "Myristylation Is Involved In Intracellular Retention of Hepatitis B Virus Envelope Proteins", *J. Virol.* 65(7): 3919–3923 (1991).

Kazuyuki et al. Novel N–Terminal Amino Acid Sequence Required for Retention of Hepatitis B Virus Glycoprotein In Endoplasmic Reticulum, *Mol. and Cell. Biol.*, 9(10): 4459–4466 (1989).

Korek et al. "Expression of Large Hepatitis B Envelope Protein Mutants Using A New Expression Vector", *Arch. Virol.* 122: 367–371 (1992).

Falkner et al. "*Escherichia coli* gpt Gene Provides Dominant Selection for Vaccinia Virus Open Reading Frame Expression Vectors", *J. Virol.* 62(6) 1849–1854 (1988).

Phalipon et al. "Genetically Engineered Diphtheria Toxin Fusion Proteins Carrying The Hepatitis B Surface Antigen", *Gene* 55: 255–263 (1987).

Zucker et al. "Monoclonal Antibody Analysis of Diphtheria Toxin—I. Localization Of Epitopes And Neutralization Of Cytotoxicity", *Molecular Immunology* 21(9): 785–793 (1984).

Nemeckova, et al., "Synthesis and Immunogenicity of Hepatitis B Virus Envelope Antigen Expressed by Recombinant Vaccinia Virus", *Arch. Virol.*, 121: 29–41 (1991).

*Primary Examiner*—Chris Eisenschenk
*Assistant Examiner*—Mary K. Zeman
*Attorney, Agent, or Firm*—Foley & Lardner

[57] ABSTRACT

The present invention relates to methods of producing recombinant molecules including the nucleotide sequence for the structure of the preS1 region of the surface glycoprotein of the hepatitis B virus, and to compositions of the molecules. Compositions of the recombinant molecules may include a promoter and a marker gene. Cloning vectors are used to incorporate the recombinant molecules into hosts. Cells infected with the chimeric vaccinia produce high levels of preS1 protein. Isolation and purification of the preS1-containing protein is facilitated by the use of a recombinant molecule in which the myristylation site has been deleted by a modification of the nucleotide sequence. The purified preS1-containing protein is useful for development of vaccines, diagnostic kits and therapies.

18 Claims, 15 Drawing Sheets

Structure of the plasmids pselP-gpt-L2/preS1 and pselP-gpt-L2/preS1dMyr

NotI and XbaI restriction maps of the wild-type and the chimeric genomes around the integration sites SacI and NotI restriction maps of the wild-type and the chimeric genomes around the integration sites Construction of the plasmid pselP-elp4gpt-L2

Structure of the plasmids pTZ-L2/preS1 and pTZ-L2/preS1dMyr

Panel B Panel A

Structures of plasmids pTZ-L2/CRM228A, pTZ-L2/preS1dMyr-CRM228A, pTZ-L2/preS2-CRM228A and pTZ-L2/sAg-CRM228A Construction of plasmid pTZ-L2/preS1dMyr(x2)

-amplify preS1dMyr sequence using plasmid pTZ-L2/preS1dMyr as a template.
-Introduce NcoI site within the binding site of PCR primer 2
-cleave PCR product with NcoI
-cleave pTZ-L2/preS1dMyr vector with NcoI, treat with CIP
- ligate vector with NcoI cut PCR product
- select for correct orientation of ligated PCR product

HIGH LEVEL EXPRESSION OF POLYPEPTIDE THAT CONTAINS MODIFIED PRES1 REGION OF HEPATITIS B VIRUS LARGE ANTIGEN

This application is a division of application Ser. No. 08/440,682, filed May 15, 1995 which is a continuation of Ser. No. 08/099,351, filed Jul. 30, 1993 now abandoned.

BACKGROUND OF THE INVENTION

Prevention and treatment of viral infections is a major medical goal. Diseases caused by non-passageable (NP) viruses are particularly intractable because the causative agents cannot be readily grown in laboratories for investigation of disease-causing mechanisms or for development of vaccines or therapies. The diseases caused by NP viruses are often quite serious, including cancers, derangement of the immune system, and debilitation.

Hepatitis B virus, or HBV, is a highly infectious NP virus of humans. In many African and Asian countries, HBV infection is endemic. Large portions of these populations are carriers of the virus and, therefore, spread of the disease is extremely difficult to control. In more developed countries, blood transfusion is one of the major modes of transmission.

HBV contains three surface glycoproteins of different size that are encoded by a single open reading frame. Each utilizes a different ATG start codon but all three employ the same TAA stop signal. Ganem & Varmus, 1987; Robinson, 1990. For HBV strain ayw, the small surface antigen, S-sAg, or major protein, contains 226 amino acids. The middle surface glycoprotein, preS2-S-sAg or middle protein has an additional 55 amino acids at the amino terminus of the S-sAg. Likewise, the large surface glycoprotein, preS1-S2-S-sAg or large protein, has 108 amino acids linked to the amino terminus of the preS2-S-sAg. The use of the terms "preS1" or "preS2" regions hereafter are references to the additional 108 and 55 amino acid segments seen in the large and middle antigens, respectively.

The large protein is myristylated at its N-terminal glycine residue. Persing et al. (1987). The molecular weight of each antigen depends on glycosylation and is 24 or 27 kD for the small protein, 30 or 33 kD for the middle protein and 39 or 42 kD for the large protein. Ganem & Varmus, 1987.

The preS regions bind to receptors on the surface of liver cells either via polymerized human serum albumin, in the preS2 region, or by direct binding of the preS1 region to the receptor molecule. Pontisso et al., 1989a; Neurath et al., 1990; Pontisso et al., 1989b; Petit et al., 1992. PreS1-S2-S-sAg remains associated with the endoplasmic reticulum (ER) and leaves the infected cell only as a component of an infectious virus particle (22 nm) or as a component of filamentous, non-infectious particles (42nm) late in infection. Hollinger, 1990. By contrast, the middle and the major antigen are secreted efficiently and assemble into infectious 22 nm particles. Mechanisms that mediate translocation of the middle and the major antigen through the membrane of the ER, or that prevent secretion of the large antigen, have been described. Ou & Rutter, 1987; Masuda et al., 1990; Prange et al., 1992.

All three HBV surface proteins induce B cell- and T cell-specific immune response in infected individuals. In approximately 90% of cases, these responses result in a complete clearance of infectious virus. Hollinger, 1990. Detailed analysis of the surface glycoproteins has identified discrete B cell- and T cell-specific neutralizing epitopes in both the major antigen and the preS regions. Neurath et al., 1985; Milich et al., 1985a; Milich et al., 1985b; Neurath et al., 1989.

Hepatitis B virus antigen consists of a group-specific antigen, a, and at least two subtype determinants, d/y and w/r (Le Bouvier, 1971; Bancroft et al., 1972) resulting in several distinct antigenic genomic subtypes: adw, ayw, adr and ayr. The geographic distribution of subtypes has been described by Nishioka et al. (1975). Subtype cross-protection has been shown by Szmuness et al. (1982). Some of the subtype-specific determinants are located in the preS regions (e.g., Milich et al., 1990a & 1990b).

Vaccination studies with several mouse strains have shown that the response to certain S-sAg epitopes is dependent on the presence of defined molecules of the major histocompatibility complex. Certain strains not responding to the major protein, however, do respond to additional epitopes in the preS regions of the large protein. Nonresponsiveness of mice to vaccines based on the major antigen alone, therefore, can be circumvented by including the large protein in vaccine preparations. Milich et al., 1985a & 1985b.

In humans, the immune response varies from nonresponding to low-responding to high-responding. This effect appears to be haplotype-dependent. Egea et al. (1991). While vaccines based on the major antigen alone are, in most cases, sufficient to induce an antibody response in humans resulting in protection from disease (Szmuness et al., 1980), a certain percentage of hosts, do not respond to S-sAg-based vaccines. In one study, 7–15% of those vaccinated with S-sAg did not respond by producing antibodies. Nowicki et al., *J. Infect. Dis.* 152: 1245–58 (1985). Vaccines partially, primarily or exclusively based on the large antigen are therefore desirable for the vaccination of patients that respond poorly to vaccines containing only the major antigen.

In some reports, combinations of antigens have been found to show improvement in responder rates, suggesting that to be most effective, a candidate vaccine should contain the antigenic components of all three surface glycoproteins. To determine the optimum combinations of antigens and optimum ratios of those antigens, it is necessary to be able to isolate and purify various antigenic components of HBV, and to have sufficient quantities to conduct appropriate research.

Despite intensive efforts in this regard, the antigenic structure and function of various HBV antigens remains largely unknown. One of the barriers to gaining information on HBV antigens is the difficulty of obtaining sufficient quantities these polypeptides. A further problem is the isolation of individual HBV components for the development of vaccines and drugs of general efficacy against a variety of infectious HBV strains.

Some components of the antigens may be painstakingly isolated from serum or tissues of infected humans or other primates, but these efforts yield unacceptably small quantities. Antigens prepared from infected cells, blood or purified virus also run the risk of contamination with active virus. Therefore, it appears that isolation and purification of antigenic components of HBV in useful quantities is feasible only by recombinant technology. Large quantities and more pure samples of antigenic components relative to those obtainable from tissues of infected individuals are expected from recombinant methods. Thus, preparation of vaccines and development of therapies should be aided by the improved production and purification capabilities afforded by in vitro expression of recombinant HBV proteins.

Expression of the small, middle and large HBV surface glycoprotein in various prokaryotic and eukaryotic expression systems has been demonstrated. Yu et al. 1990; Lin et al. 1991; Schödel et al. 1991; Kumar et al. 1992. These systems include yeast (Dehoux et al. 1986; Imamura et al. 1987; Shiosaki et al. 1991; Kuroda et al. 1992), mammalian cells (Ou & Rutter, 1987; Lee et al. 1989; Youn et al. 1989; Korec et al. 1992) and viral expression systems (McLachlan et al. 1987; Yuasa et al. 1991; Shiraki et al. 1991; Belyaev et al. 1991). However, yeast expression systems produce overglycosylated HBV large antigens and non-glycosylated major proteins, neither of which are secreted. Prokaryotic systems do not glycosylate polypeptides nor do they secrete recombinant proteins.

The current system for commercial expression of HBV surface glycoproteins for the production of vaccines involves a yeast expression system that constitutively expresses these proteins. Transformed yeast cells produce the small HBV surface glycoprotein with characteristics similar to the 22 nm particles seen in the blood of naturally-infected persons. The major protein produced in yeast, however, is not glycosylated (see EP 0 414 374 A2, p. 16), while the large antigen is overglycosylated. To overcome this disadvantage, large antigens with deleted glycosylation sites have been constructed (EP 0 414 374 A2, Example F.3). Such modifications, however, are likely to reduce the natural immunogenicity of the antigen.

In natural infections with HBV, the large surface glycoprotein is translated from a preS1-specific mRNA, whereas the middle and the small protein are translated from a preS2-specific mRNA (Robinson 1990). The transcriptional promoter elements for the preS1-S2-S gene are located upstream of this gene while the preS2-S gene has its own promoter elements located within the preS1 region. In transformed cell lines containing an integrated preS1-S2-S gene, both the preS1-S2-S 2.4 kB mRNA and the preS2-s 2.1 kB mRNA are transcribed, and all three antigens are expressed. Permanent cell lines having incorporated the preS1-S2-S gene secrete particles consisting predominantly of the major S antigen with varying amounts of the M and the L antigen (PCT WO 90/10058). HBV surface glycoproteins expressed in eukaryotic cells are secreted more efficiently, but the yield of recombinant protein is less than in prokaryotes or yeasts. Thus far, only Chinese Hamster Ovary (CHO) cells have shown continuous expression of recombinant HBV surface glycoprotein genes. Ou & Rutter, 1987; Lee et al., 1989; Youn et al., 1989; Korec et al., 1992.

In the vaccinia virus expression system, HBV surface glycoproteins have been expressed mainly under the control of the weak vaccinia P7.5 promoter. Since expression levels using this promoter are low, the large antigen has been detected only using sensitive detection methods such as radioactive labeling and autoradiography. Cheng et al., 1986; Cheng et al., 1987; Kutinivà et al., 1990; Nemeckovà et al., 1991. It was reported that expression of the small and middle antigens in a vaccinia virus system results in a efficient secretion of both polypeptides. Cheng et al., 1987. The large antigen expressed via vaccinia virus, however, is not secreted, but remains associated with intracellular membranes. Cheng et al., 1986.

In an effort to improve results using vaccinia virus as an expression vehicle, Fuerst et al. (1987) replaced the normal P7.5 promoter with a bacteriophage T7 promoter. In addition, a T7 RNA polymerase gene was incorporated into a separate plasmid or virus to facilitate transcription from the heterologous T7 promoter. The results showed that with three different proteins, *E. coli* β-galactosidase, HBV small antigen and HIV gp160, expression from a T7 promoter by a T7 polymerase was higher than that seen with native vaccinia promoters.

Elroy-Stein et al. (1989) provided yet another variation on the vaccinia virus expression system. Using the hybrid T7/vaccinia system described above, they further included an encephalomyocarditis virus 5' untranslated region (UTR) to help improve translation of the RNA produced by the T7 polymerase. The results showed improved expression of a recombinant chloramphenicol transferase (cat) gene with protein levels approaching 10% of total cell protein.

An interesting result of cloning of the preS1-preS2-S-sAg gene into a vaccinia expression vector is expression of the large antigen without expression of the small or middle antigens. This is in contrast to transformed cell lines where all three antigens are expressed from the preS1-preS2-S-sAg gene. Thus, the present invention shows that vaccinia systems allow for the expression of pure preparations of the large protein alone, increasing the content of the important preS1-region epitopes.

In contrast to virtually all other reports, Li et al., U.S. Pat. No. 5,077,213, demonstrates that a recombinant vaccinia virus (strain Guang), carrying the preS1-S2-S gene from HBV strain adr, drives the efficient secretion of small, middle and large antigen from $TK^-$ osteosarcoma cells infected with this recombinant. It is not apparent from Li et al. what factors account for the reported results when in other reports, vaccinia is (i) shown not to secrete large antigen and (ii) fails to produce small and middle antigens from the native HBV promoter. In addition, it is difficult to discern any general principle(s) in this regard because Li et al. used neoplastic (osteosarcoma) cells as hosts. The unusual characteristics of these cells may well be responsible for the different results reported by Li et al.

SUMMARY OF THE INVENTION

The present invention provides a method for the production of an HBV preS1-containing antigen using a vaccinia virus expression vector. The removal of the myristylation site at the amino-terminus of the HBV large antigen provides significantly higher levels of expression for proteins derived therefrom. Expression of the demyristylated antigen in vaccinia virus can be achieved (i) using a strong vaccinia promoter or (ii) using a bacteriophage T7 promoter sequence and RNA polymerase to facilitate transcription of the preS1 antigen. The demyristylation of recombinant HBV large antigen results in levels of expression that would not have been predicted by the prior art. Optionally, HBV large antigen may be combined with an immunopotentiator. In the case of a polypeptide immunopotentiator, the large antigen may be coupled via a chemical linkage or by recombinant methods, i.e., splicing DNA sequences encoding the immunopotentiator and HBV large antigen to produce a new hybrid gene. Finally, the use of a the vaccinia virus expression system permits the use of cells in which HBV replication normally occurs as hosts. The resulting availability of large quantities of purified HBV large antigen, processed in a "natural" fashion, permits a wide range of diagnostic, therapeutic or vaccine regimes that were heretofore unattainable.

Therefore, it is an object of the present invention to provide a DNA sequence encoding a preS1-containing antigen that lacks the myristylation site present in the preS1 region of the HBV large antigen. The myristylation site can be destroyed by site-specific mutagenesis of the residue at which myristylation takes place or by deletion of the site in whole. The construct then can be cloned into the genome of a first chimeric vaccinia virus vector under the control of a vaccinia regulatory sequence. After infection of cells with the vector, the demyristylated protein is synthesized at high levels.

It is another object of the present invention to provide a chimeric vaccinia virus vector that has a demyristylated version of a preS-containing antigen under the control of a bacteriophage T7 promoter. A second chimeric vaccinia virus vector encodes the bacterial T7-phage RNA polymerase. By coinfecting cells with both the first and second viruses, preS1-containing antigen is produced at high levels.

Still another object of the present invention is to provide a preS1-containing antigen according to the previous objectives where the antigen is produced by infection of liver- and kidney-derived cell. Thus, the antigen will be processed in a manner consistent with maintenance of its natural antigenicity and immunogenicity.

It is also an object of the present invention to provide a preS1-containing antigen in a purified or partially purified form. Obtaining such antigen is more easily accomplished in a vaccinia-based expression system where the internal promoter generating for the small/middle antigen transcript is not active. Therefore, no small or middle antigens are produced.

A further object of the present invention is to provide a preS1-containing vaccine according to the previous objectives. The importance of such a product is demonstrated by the ability of the preS1 region to confer immunity on a significant minority of persons that fail to respond to standard HBV vaccines.

It is yet another object of the present invention to provide a preS1-containing vaccine that also contains an immunopotentiator coupled thereto by fusion of preS1- and immunopotentiator-coding sequences or by chemical coupling.

Another object of the present invention is to provide a preS1-containing antigen wherein more than one copy of the preS1 region is present.

In satisfying the foregoing objectives, there is provided, in accordance with one aspect of the present invention, a chimeric vaccinia virus is provided that comprises a promoter operationally linked to a polynucleotide that encodes a portion of an hepatitis B virus large antigen that contains at least one preS1 B- or T-cell epitope, wherein said portion lacks the myristylation site of the preS1 region.

According to another aspect of the invention, a method for the synthesis of a hepatitis B virus antigen is provided, comprising the steps of (a) infecting a suitable eukaryotic cell with a first chimeric vaccinia virus which comprises a promoter operationally linked to a polynucleotide that encodes a portion of the preS1 protein region of a hepatitis B virus large antigen that contains at least one preS1 B- or T-cell epitope, wherein said portion lacks the myristylation site of the preS1 region; (b) culturing the coinfected cell; (c) lysing the coinfected cell; and (d) harvesting said antigen.

Pursuant to one preferred embodiment of the present invention, a hepatitis B virus antigen is produced by a method comprising the steps of (a) coinfecting a suitable eukaryotic cell with a first chimeric vaccinia virus which comprises a promoter operationally linked to a polynucleotide that encodes a portion of the preS1 protein region of a hepatitis B virus large antigen that contains at least one preS1 B- or T-cell epitope, wherein said portion lacks the myristylation site of the preS1 region; (b) culturing the coinfected cell; (c) lysing the coinfected cell; and (d) harvesting said antigen.

In another preferred embodiment, the hepatitis B virus antigen is linked to an immunopotentiator.

In yet another embodiment, there is provided a vaccine comprising an antigen of hepatitis B virus produced by the method described above in a pharmaceutically acceptable carrier.

In yet another embodiment, there is provided an anti-HBV preS1 antibody produced by immunizing a mammal with an antigen of hepatitis B virus produced by the method described above.

In addition, diagnostic kits comprising either a hepatitis B virus antigen or an anti-HBV preS1 antibody are provided.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this disclosure.

Figure 7:
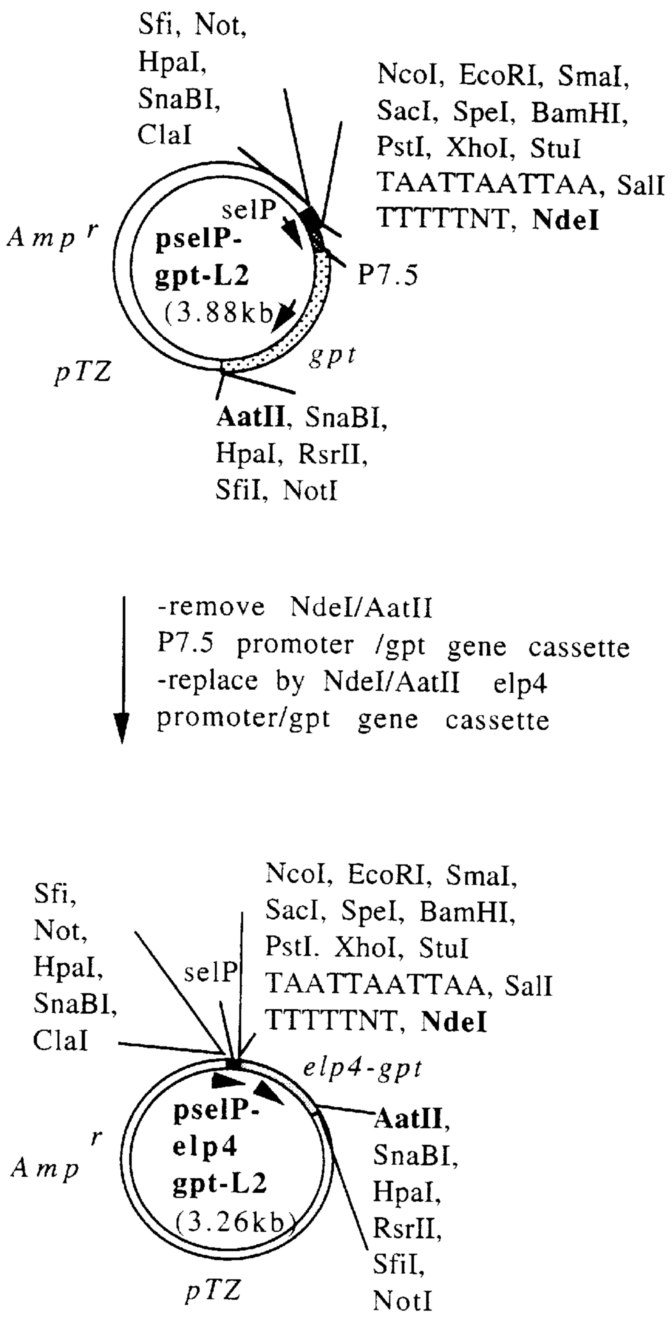

FIG. 7—Construction of the plasmid pselP-elp4gpt-L2. The vaccinia virus P7.5 promoter (P7.5) or the synthetic vaccinia early/late promoter 4 (elp4) controls the *Escherichia coli* xanthine guanine phosphoribosyltransferase (gpt) gene. Arrows indicate the direction of transcription.

Figure 8:
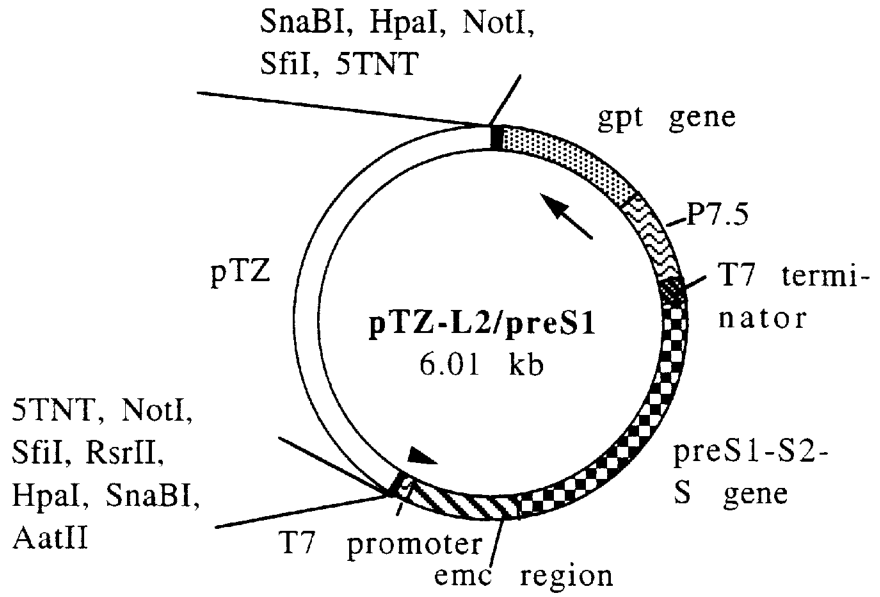
Figure 8:
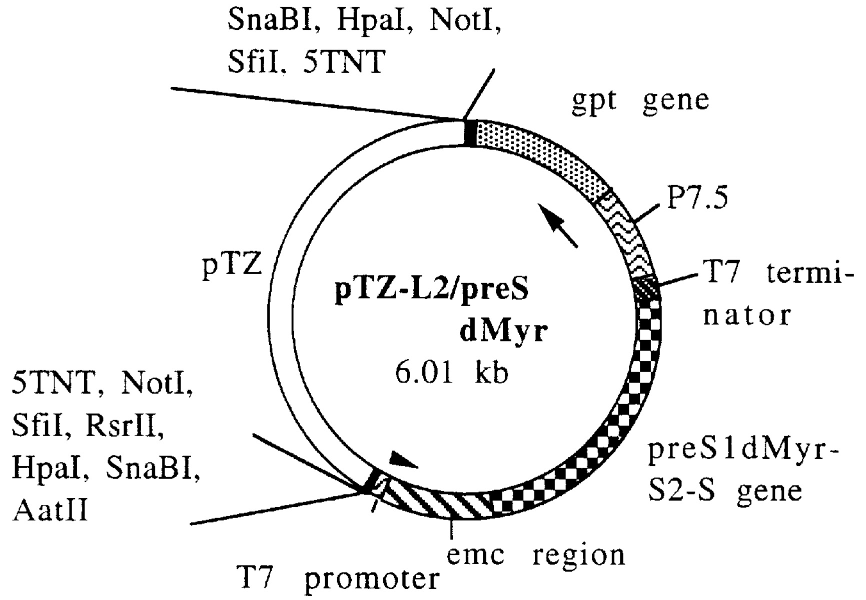

FIG. 8—Structure of the plasmids pTZ-L2/preS1 and pTZ-L2/preS1dMyr. The genes coding for the HBV large protein (preS1) or its demyristylated version (preS1dMyr) were placed under the control of the bacteriophage T7 promoter linked to a DNA copy of the Encephalomyocarditis Virus (emc) 5'-non-coding region. For further abbreviations see legend of FIG. 7. Arrows indicate the direction of transcription.

Figure 9:
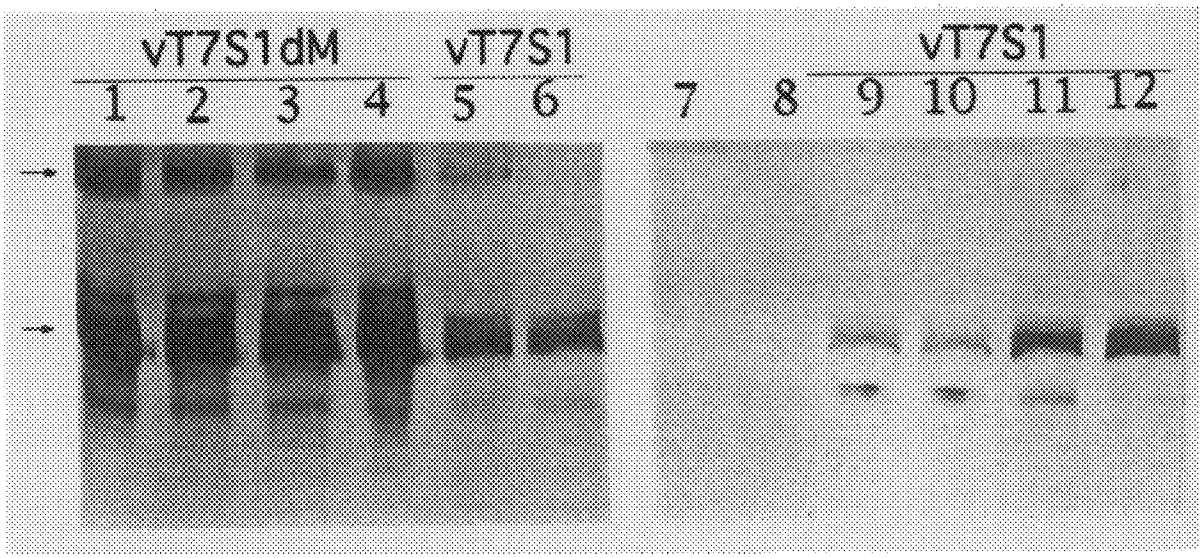

FIG. 9—Western blots of total proteins extracted from cells coinfected with the T7 polymerase expressing virus vT7/selP and the viruses vT7S1 or vT7S1dM. Lanes 1–4: lysates from CV-1 cells infected with vT7S1dM #1–4. Lanes 5 and 6: lysates from CV-1 cells infected with vT7S1 #1 and 2. Lane 7: lysate from wild-type vaccinia virus infected CV-1 cells. Lane 8: lysate from mock-infected CV-1 cells. Lanes 9–12: lysates from CV-1 cells infected with vT7S1 #3–6. Arrows indicate the monomeric large antigen (lower arrow) and aggregated forms of the antigen (upper arrow).

Figure 10:
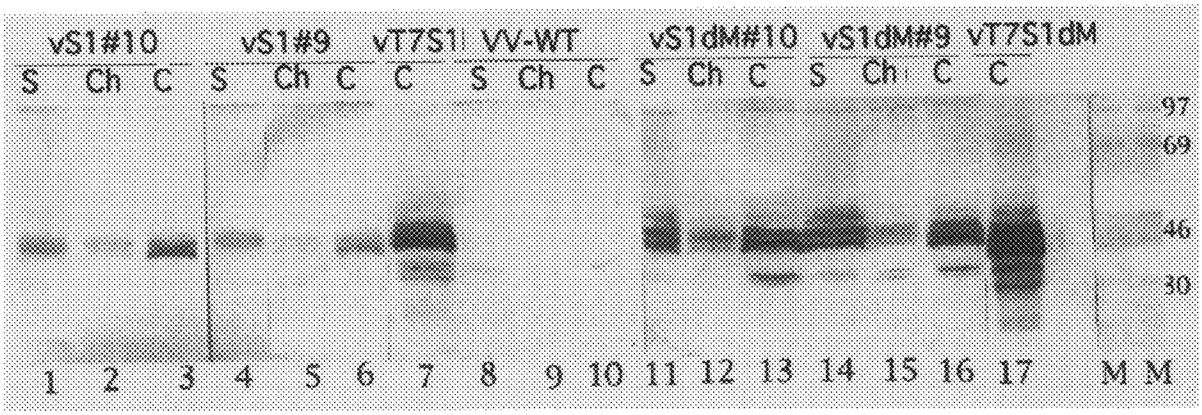

FIG. 10—Western blots of total proteins of different cell lines infected with different chimeric viruses. Lanes 1–3: lysates from SK-Hep1 (S), Chang liver (Ch) or CV-1 (C) cells infected with vS1 #10. Lanes 4–6: lysates from SK-Hep1, Chang liver or CV-1 cells infected with vS1 #9. Lane 7: lysate from CV-1 cells infected with a vT7S1 #1. Lanes 8–10: lysates from SK-Hep1, Chang liver or CV-1 cells infected with wild-type vaccinia virus. Lanes 11–13: lysates from SK-Hep1, Chang liver or CV-1 cells infected with vS1dM #10. Lanes 14–16: lysates from SK-Hep1, Chang liver or CV-1 cells infected with vS1dM# 9. Lane 17: lysate from CV-1 cells infected with vT7S1dM #1.

Figure 11:
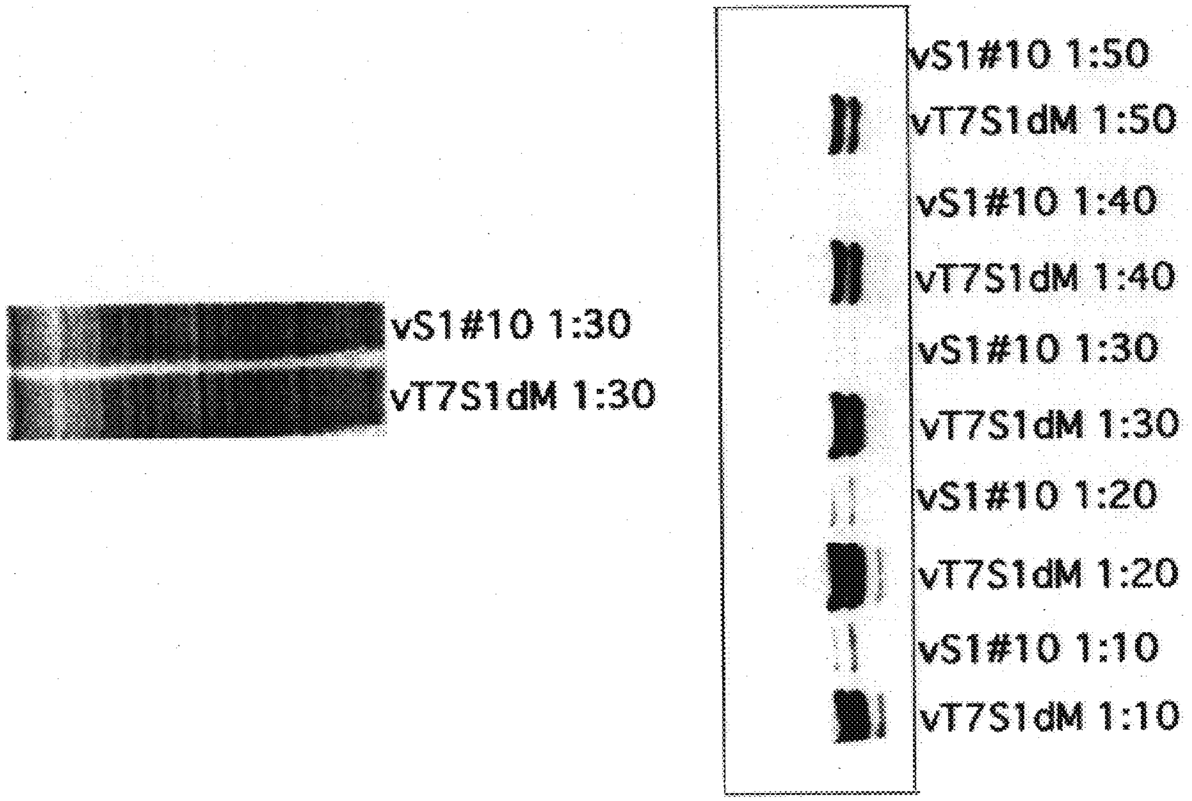

FIG. 11—Western blots of total proteins from cells infected with chimeric viruses expressing myristylated and demyristylated antigens. FIG. 11, Panel A shows the preS1 specific immune staining signals in a Western blot of lysates of 1:10, 1:20, 1:30, 1:40 and 1:50 dilutions. Differing dilutions were necessary to determine the immune staining signal suitable for the evaluation in a densitometric scanning system. To demonstrate identical amounts of total protein in the lysates, a Coommassie Blue staining of the 1:30 dilution of lysates from vS1#10 and vT7S1 infected CV-1 cells is shown in FIG. 11, Panel B.

Figure 12A:
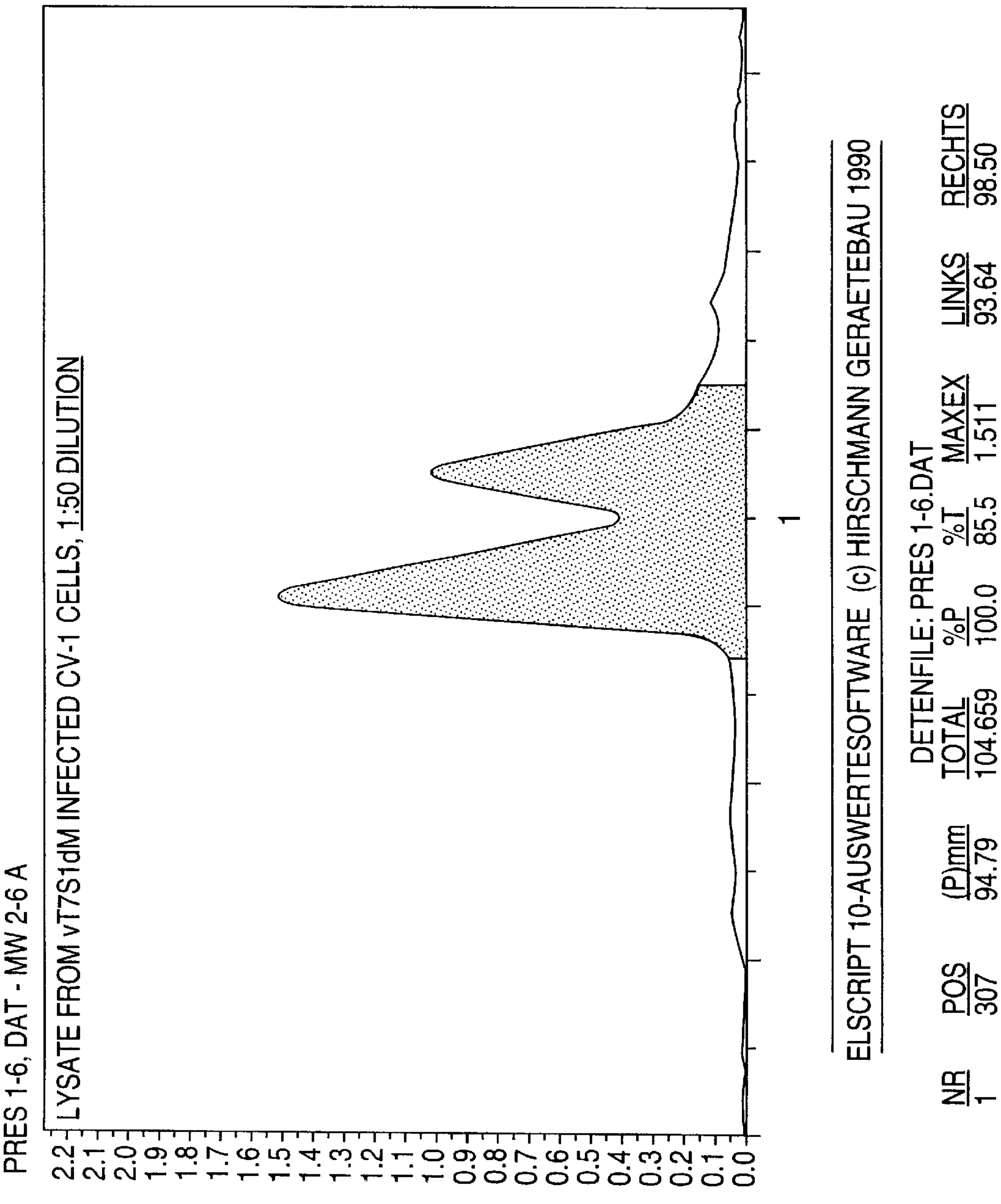
Figure 12B:
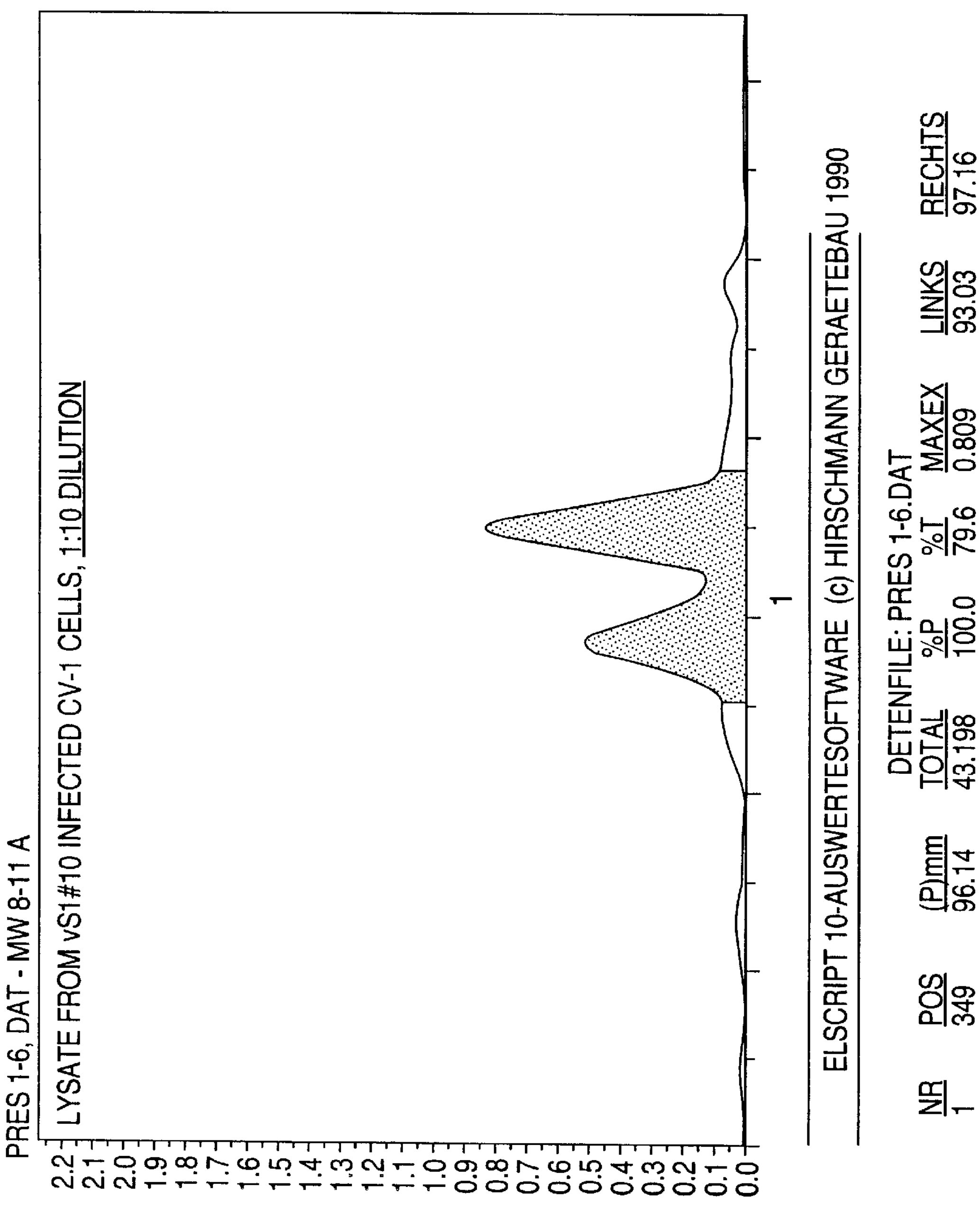

FIG. 12A and 12B—Densitometric scans of Western blots of total proteins from cells infected with chimeric viruses expressing myristylated and demyristylated large antigens. Computer-generated graphics of the densitometric scanning of vT7S1dM- and vS1#10-infected CV-1 cells. A dilution of 1:50 was employed for the T7/modified construct and 1:10 for the selP/wild-type construct. The shaded area under the curve is calculated and given under "Total" at the bottom of each panel.

Figure 13:
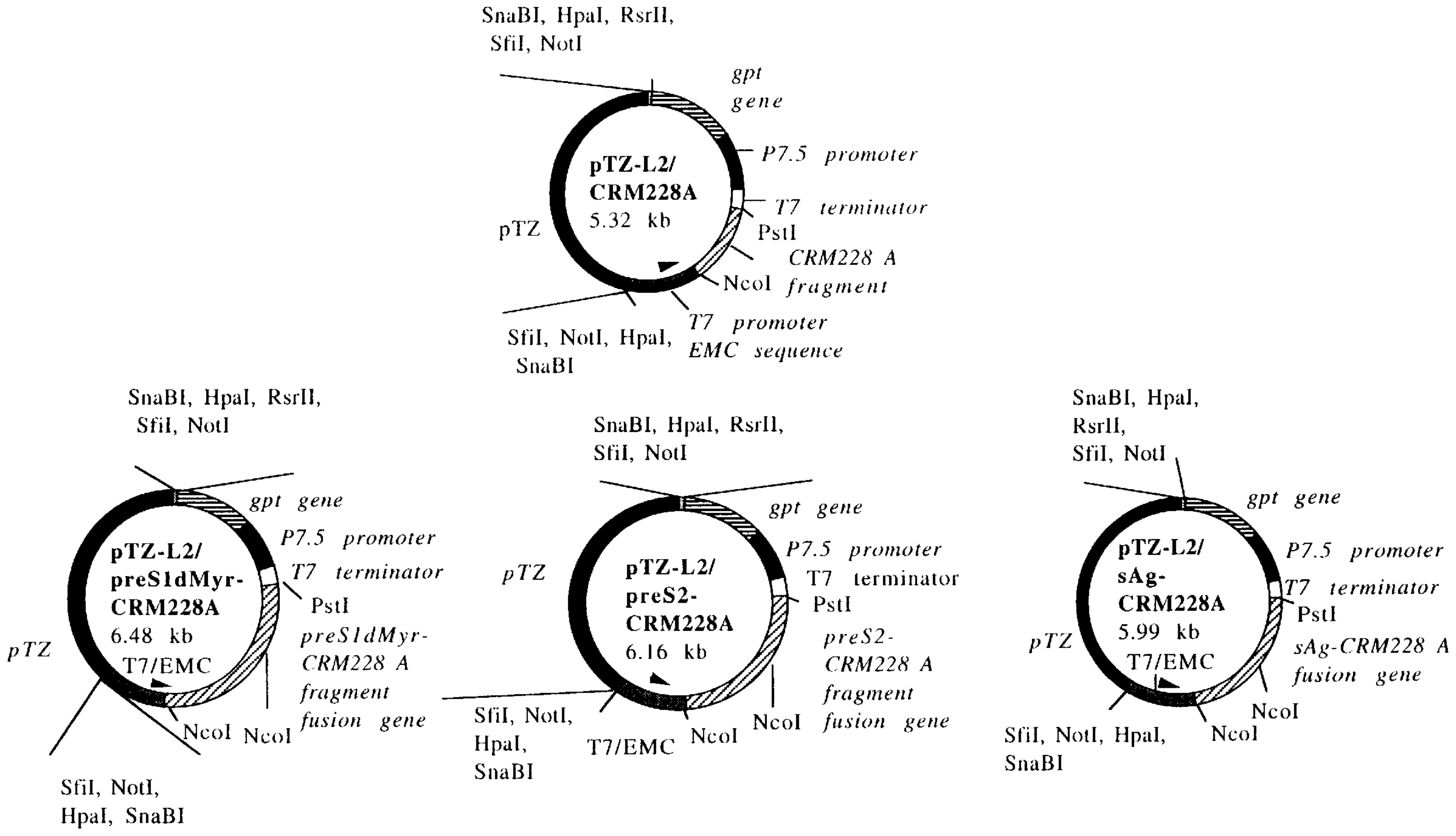

FIG. 13—Structure of the plasmids pTZ-L2/CRM228A, pTZ-L2/preS1dMyr-CRM228A, pTZ-L2/preS2-CRM228A and pTZ-L2/sAg-CRM228A. The nucleotide sequence coding for the A fragment of the Corynebacteriophage beta tox 228 gene is fused in frame as a NcoI/PstI fragment with the complete open reading frames of the HBV ayw preS1-preS2-S-sAg gene, the preS2-S-sAg gene or the S-sAg gene. The fused genes are placed under the transcriptional control of a modified bacteriophage T7 promoter. The direction of transcription is indicated by arrows.

Figure 14:
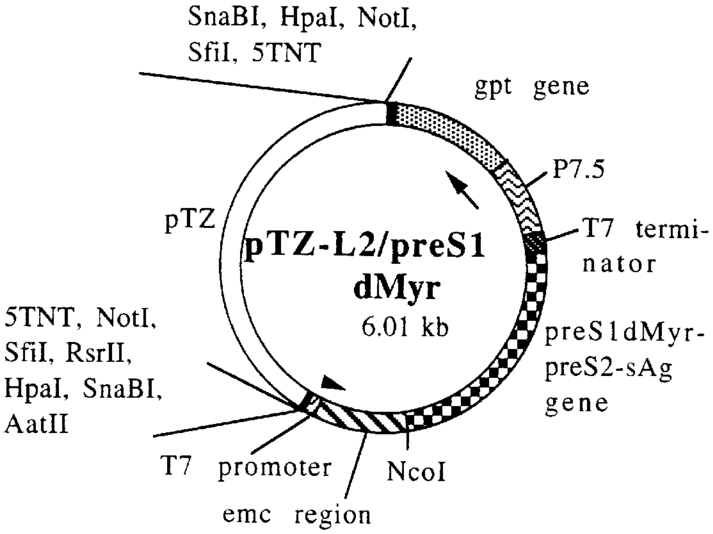
Figure 14:
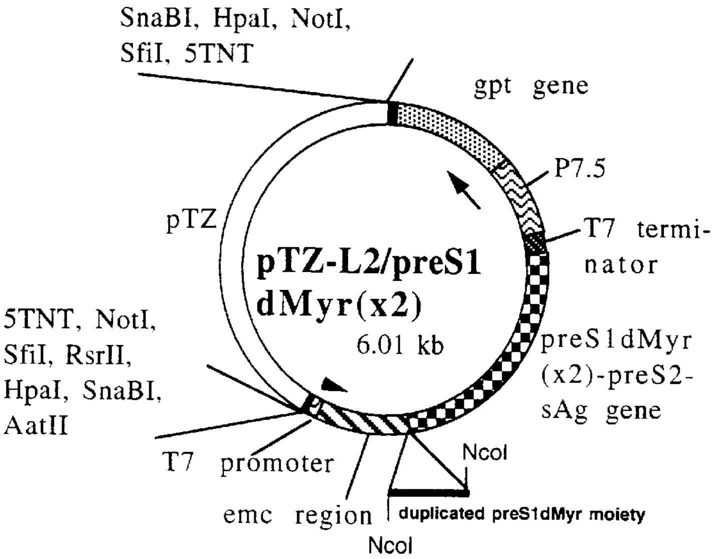

FIG. 14—Construction of the plasmid pTZ-L2/preS1dMyr (×2). The nucleotide sequence of the preS1 moiety (nucleotides 1–324) of the preS1dMyr-preS2-sAg gene was amplified using plasmid pTZ-L2/preS1dMyr as a template and specific PCR primers. The PCR product was cloned as a NcoI fragment into a NcoI-cut, calf intestinal phosphatase-treated pTZ-L2/preS1dMyr vector. The preS1-preS1-preS2-sAg gene is placed under the transcriptional control of a modified bacteriophage T7 promoter. The position of the PCR primers and the direction of transcription is indicated by arrows.

DETAILED DESCRIPTION OF PREFERRED EMBODIMENT

A recombinant nucleotide molecule is constructed which includes the sequence encoding the structure of the preS1 region of the HBV large antigen. To isolate the large antigen structural gene, Dane particle DNA provides a ready source from which components of the HBV genome may be isolated using standard methods known to those skilled in the art. In general, the construction entails isolating the Dane particle DNA, cleaving the DNA with enzymes, identification of DNA fragments that contain the large antigen structural gene, recombining the isolated gene with a cloning vector, recombining part of the cloning vector, including the preS1 region, into a vaccinia virus vector, and infecting a suitable host with the chimeric vaccinia virus. The chimeric vaccinia is capable of replicating within the host and expressing both vaccinia and non-vaccinia genes. Infected cells express a preS1-containing protein.

Chemical synthesis may also be used to generate the necessary DNA sequences. Oligonucleotides may be synthesized using apparatus such as that of Applied Biosystems, e.g., Model 380A, or by chemical techniques such as that the method of Matteucci et al., *J. Am. Chem. Soc.* 103:3185–3191 (1981). DNA sequences coding for proteins of HBV may be isolated from Dane particles using methods such as those described by Robinson, *Am. J. Med. Sci.* 270:151–59 (1975).

The amino-terminal myristylation site of HBV large antigen is believed to result in binding of the protein to components of the cell, notably to cell membranes. Unexpectedly, it now appears that a G-to-C transversion at the fifth nucleotide of the preS1 coding region, intended to destroy the myristylation site, also results in greater translational efficiency and, hence, increased yields of large antigen. See FIG. 11 FIGS. 12A and 12B and Example 4.

Preferably, the chimeric virus also contains a marker gene, and cells infected with such a virus express a selectable marker protein. By adding a marker gene to the chimeric vaccinia virus, along with other sequences of interest, vectors or cells carrying the sequences may be identified and separated from those cells or vectors without them. This selection is accomplished by culturing the cells in an environment that favors growth of viruses having the marker gene.

In the present invention, the structural gene is placed under the control of a promoter. Vaccinia virus has unique transcriptional regulatory signals that are recognized by the viral RNA polymerase. Therefore, defined vaccinia promoter sequences are usually ligated to the coding sequences of interest. A strong vaccinia promoter like selP is preferred in this context.

The present invention, however, also comprehends the use of a non-vaccinia virus promoter. The promoter of choice is derived from the bacteriophage T7. The vaccinia virus-bacteriophage T7 hybrid expression system has been shown to substantially improve expression of several foreign genes. Elroy-Stein et al. (1989). Since vaccinia virus transcriptional machinery does not act on this promoter, the present invention also provides a T7 RNA polymerase. Thus, the structural gene is operatively-linked to a regulatory element from the phage, which regulatory element is acted upon by a phage polymerase. In the preferred embodiment, the promoter/HBV large antigen gene and the T7 RNA polymerase gene are contained in different chimeric vaccinia viruses and are brought into contact by coinfection of the same cell.

A "cassette" is a covalently-connected series of DNA codons which code for multiple, non-overlapping proteins. In the present invention, a cassette will include a preS1-containing gene and may also encode a marker gene. The cassette will also contain a promoter sequence derived from the T7 phage. Normally, cassettes are flanked by unique restriction sites that allow for excision from and recombination into a variety of cloning vectors, and in this case, genetically-engineered vaccinia viruses.

A cloning vector is used as an intermediate carrier of the isolated gene. Preferably, the cloning vector contains a promoter and a marker gene that can be used to generate a cassette for direct transfer into a recipient the vaccinia virus genome. Incorporation of the cassette into the vaccinia sequences requires cleaving of both the preS1-containing cloning vector and the viral genome, the latter generally being cut at a preferred site relative to vaccinia virus genes. The next step is ligation of the excised or linearized cassette with the vaccinia genome. This results in the formation of a linear, chimeric viral genome. Subsequently, the ligated DNA is transfected into cells infected with a second vaccinia virus that supports the packaging of the chimeric DNA into an infectious viral particle.

The production of a preS1-containing protein, according to the present invention, includes the steps of (i) initiating a cell culture and (ii) infecting the culture with one or more chimeric vaccinia viruses. The cells must be permissive for replication of vaccinia and could include mammalian kidney cells lines like Vero (ATCC #CCL81) and CV-1 (ATCC #CCL70) and liver cell lines like SK-HEP-1 (ATCC #HTB52) and Chang (ATCC #CCL13).

One advantage of the vaccinia virus system is its wide range of suitable hosts, including liver cells, kidney cells and many other mammalian cell lines. This property has not yet been exploited for the expression of recombinant HBV surface glycoproteins. Since post-translational processing and modification is an important aspect of the immunological properties of an antigen, the most desirable expression system for this type of vaccine involves a mammalian cell, preferably liver and kidney cells.

Viewing the relevant art, one must question the "quality" of antigen derived from certain host cells in terms of potential vaccines. Without proper protein processing, even large amounts of antigen are of little value. Therefore, according to the present invention, host cells preferably are not only permissive but representative of the kinds of cells in which HBV normally replicates. Hence, they are capable of producing HBV antigens that closely resemble those produced during a natural infection. The cultured cells should be able to provide the post-translational modifications that permit recombinant antigens to express natural, antigenic and immunogenic epitopes. Cells of liver and kidney origin are the most preferred in this respect.

Cultures are incubated under conditions that optimize the expression of the recombinant proteins. Variables that would be optimized include, but are not limited to time, temperature, pH, $CO_2$ concentration, presence of serum proteins, growth factors, and nutrients. Usually, a selective factor that favors the growth of viruses carrying recombinant genes is also included. The expression of the protein is optimal, usually when a maximum amount of protein has been produced. Infected cells may be mechanically, chemically or thermally disrupted to increase the yield of the product.

Optionally, the recombinant product is further purified as required for a given application. Methods for purification of polypeptides from cell culture are known to those of skill in the art. Techniques that may be employed include salt extraction, gradient centrifugation, gel filtration, gel chromatography, ultrafiltration, electrophoresis, ion exchange and the like.

Not all proteins, in and of themselves, prove to be effective immunogens. In order to enhance whatever inherent immunogenicity a particular protein might have, it is often advisable to couple the protein of interest to an immunopotentiator. There are several classes of immunopotentiators including fat-based vehicles (Freund's Adjuvant), aluminum agents (Alum), toxins (lipid A) and proteins (interleukins).

In one particular embodiment, immunopotentiators are toxins that can be chemically, or in the case of protein toxins, genetically linked to immunogens. Potential toxins for use in such constructs include, but are not limited to ricin, abrin, Pertussis toxin, Shigella-like toxin, Cholera toxin, Staphylococcus exotoxin A, heat-stable and heat-labile Enterotoxin and Pseudomonas exotoxin A. In some cases, it is desireable to reduce the toxicity of the toxin moiety by chemical or genetic means. Revillard et al., *Devel. Biol. Stand.* 77:31 (1992); Perentesis et al., *Biofactors* 3:173 (1992); Haslov et al., *Immunobiology* 183:40–54 (1991); Hussain et al., *Nat. Immun. Cell Growth Reg.* 8:231–44 (1989).

Diphtheria toxin is shown here, for the first time, to be effective at immunopotentiating an immunogen to which it is coupled. Previously, the use of diphtheria toxin in fusion constructs as an immunotoxin has been reported. Strom et al., *Ann. N.Y. Acad. Sci.* 636:233–50 (1991); Shaw et al., *J. Biol. Chem.* 266:21118–24 (1991); Williams et al., *J. Biol. Chem.* 265:11885–89 (1990). Immunotoxins differ from immunpotentiators, however, in that the former is a toxin/antibody fusion molecule that selectively destroys target cells while the latter is a toxin or a toxin/protein fusion molecule where the toxin moiety enhances the immugenecity of the antigen moiety. The use of toxins other than diphtheria toxin as immunopotentiators has been reported: cholera toxin, Hussain et al. (1989); pertussis toxin, Halsov et al. (1991).

Two methods of coupling are possible for protein toxins. First, chemical cross-linking agents can be used to physically attach the protein immunogen to a protein immunopotentiator. The methods for chemical coupling are well-known to those of skill in the art. For example, see articles by Feeney, *Int. J. Peptide Protein Res.* 29:145–161 (1987); Peters and Richards, *Ann. Rev. Biochem.* 46:523ff (1977); Erlanger, *Meth. Enzymol.* 70:85ff (1980); Han et al., *Int. J. Biochem.* 16:129ff (1984). Second, nucleic acid sequences encoding a protein immunogen can be spliced to nucleic acid sequences encoding the immunopotentiator. Expression of the resulting "hybrid" gene would result in a single polypeptide containing both immunogen and immunopotentiator domains.

Another method of increasing the immunogenicity of preS1 protein sequences is to provide a greater effective dosage of the epitopes contained therein. One way this can be accomplished by duplication of the preS1 sequences in HBV large antigen. By inserting at least a second copy of preS1-coding sequences into the preS1-containing construct, the protein expressed therefrom will have at least twice as many preS1 B- and T-cell epitopes. This higher epitope density can help stimulate the anti-preS1 response.

The overall result of the aforementioned methods for production of HBV preS1-containing antigens is to generate a suitable material for an improved HBV vaccine. A significant portion (7–15%) of the population does not respond to HBV vaccines that do not contain preS1 regions. The ability to immunize persons with antigens containing this region, processed in a manner consistent with a natural infection, will permit a greater number of persons to be protected from HBV infection.

Antibodies directed toward the recombinant preS1-containing protein also are encompassed by the present invention. At least three major obstacles exist that have interfered with the production of HBV preS1-specific antibodies. First, large quantities of this protein have not generally been available. Second, when significant amounts of recombinantly produced HBV antigens have been available, the mix of small, middle and large antigens dilutes the contribution of the preS1 regions. And third, recombinant preS1 polypeptides have not been produced subject to the post-translational modifications seen in naturally-infected cells. The present invention provides large quantities of preS1-containing antigens that are processed by cell-types normally infected with HBV. Therefore, the potential for production of both polyclonal and monoclonal antibodies, useful in detection, therapy and prevention of HBV-related disease, is markedly improved.

One particular use of HBV-specific monoclonal antibodies is as immunotoxins. Immunotoxins are hybrid protein molecules created by the fusion of an antibody and a toxin that can be used to selectively destroy certain cell populations. The potent cytocidal action of a toxin is tied to the exquisite specificity of monoclonal antobides, thereby effecting selective destruction of target cells while sparing other cells. Examples of such toxins include, but are not limited to ricin, abrin, Pertussis toxin, Shigella-like toxin, Cholera toxin, Staphylococcus exotoxin A, heat-stable and heat-labile Enterotoxin, Pseudomonas exotoxin A and *diphtheria* toxin. In some cases, it is desireable to reduce the toxicity of the toxin moiety by chemical or genetic means.

Fusion of toxins to antibodies can be effected chemically or, in the case of protein toxins, genetically. Genes protein toxins can be cloned in a head-to-tail fashion to single-chain antibody genes (light-chain/heavy-chain hybrids; see Huston et al., *Proc. Nat'l Acad. Sci USA* 85:5879–5883 (1988) and Bird et al., *Science* 242:423–426 (1988)). Alternatively, other binding proteins such as receptors or receptor ligands, e.g., IL-2, may be substituted for the single-chain antibody moiety.

To effect prevention of HBV disease, a vaccine comprising at least the preS1 region of HBV, produced by recombinant technology as disclosed herein, is comprehended. The vaccine includes an effective amount of preS1-containing proteins, produced by the recombinant expression systems in chimeric vaccinia-infected cells, that display suitable immunogenicity in a pharmaceutically acceptable carrier. Suitable immunogenicity means that the polypeptide is capable of eliciting an immune response that protects against a natural HBV infection.

For detection of HBV disease, a kit comprising a container and (i) at least one antibody directed to a preS1-containing molecule or (ii) a preS-containing molecule is contemplated. Detection of a preS1-containing molecule produced by natural infection involves antibodies of the present invention. Detection of preS1-specific antibodies produced by host against a natural infection or immunization involves the preS1-containing molecules of the present invention. In both cases, an antibody with a chromatographic, fluorometric or other detectable labels is used to detect either the preS1-containing protein or a preS1-specific antibody. Preferably, the kit also comprises a positive control for the binding of a preS1-containing molecule to a preS1-specific-antibody, or vice versa, as well as the detection reaction.

The present invention also relates to a method for producing proteinaceous particles displaying HBV antigenicity and/or immunogenicity. Culturing of infected cells results in the production of proteinaceous particles. The particle-containing cells are then recovered. In preferred embodiments the particles are isolated from the cells using a variety of methods well known to those skilled in the art.

EXAMPLE 1

Construction of Cloning Vectors pselP-gpt-L2/preS1. The 1447 base pair NsiI (position 1070 in the HBV ayw genome) to BstEII (position 2817 in the HBV ayw genome) fragment was isolated from the plasmid pTHBV. Christman et al., 1982. Overhangs resulting from the restriction endonuclease digests were removed using T4 DNA polymerase. The blunt ended fragment was cloned into the SmaI cut and dephosphorylated vector pTM3 (Moss et al., 1990) resulting in the intermediate plasmid pTM3/preS1A carrying a correctly orientated insert. The bacterial clone carrying the plasmid pTM3/preS1A was infected with a M13 helper phage (Stratagene, Heidelberg, FRG) to obtain single strand (ss) plasmid DNA. This ss DNA was used to create a NcoI site around the preS1 ATG start codon by site directed mutagenesis (mutagenesis oligonucleotide, 5'-GGA AAG ATT CTG CCC CAT GGT GTA GAT CTT GTT-3'). The intermediate plasmid was named pTM3/preS1B. This manipulation allowed the removal of a 40 bp NcoI fragment containing 5'-non-coding sequences from pTM3/preS1B. The remaining vector was purified and religated via the NcoI sites resulting in pTM3/preS1C. The 1418 NcoI/PstI fragment, containing the complete preS1-S2-S-sAg gene without 5'-non-coding sequences was isolated from the plasmid pTM3/preS1C and ligated with the NcoI/PstI cut pselP-gpt-L2 vaccinia virus cloning vector. See U.S. Pat. No. 5,445,953. The resulting plasmid was named pselP-gpt-L2/preS1.

pselP-gpt-L2/preS1dMyr. The ss DNA, prepared from the plasmid pTM3/preS1A was used to create a NcoI site around the preS1 ATG start codon by site directed mutagenesis using mutagenesis oligonucleotide, 5'-GGA AAG ATT CTG CGC CAT GGT GTA GAT CTT GTT-3', that simultaneously introduced a C-residue at position 2 of the second codon changing the glycine residue at the N-terminus of the preS1-S2-S open reading frame to an alanine residue (pTM3/preS1dMyrA). The resulting 40 base pair NcoI fragment containing 5'-non-coding sequences was removed and the remaining vector was purified and religated via the NcoI sites, resulting in plasmid pTM3/preS1dMyrB. The 1418 NcoI/PstI fragment, containing the complete modified preS1-S2-S-gene without 5'-non-coding sequences was isolated from pTM3/preS1dMyrB and ligated with the NcoI/PstI cut pselP-gpt-L2 vaccinia virus cloning vector. See U.S. Ser. No. 07/750,080. The resulting plasmid was designated pselP-gpt-L2/preS1dMyr.

pTZ-L2/preS1. To obtain the plasmid pTZ-L2/preS1 the NcoI/PstI cassette from pTM-3/preS1C was ligated with the NcoI/PstI cleaved pTZ-L2 vector. See U.S. Pat. No. 5,445, 953.

pTZ-L2/preS1dMyr. To obtain the plasmid pTZ-L2/preS1dMyr, the NcoI/PstI cassette from pTM-3/preS1dMyrB was ligated with the NcoI/PstI cleaved pTZ-L2 vector. See U.S. Ser. No. 07/750,080.

pselP-elp4gpt-L2. To replace the vaccinia virus P7.5 promoter from pselP-gpt-L2 by a synthetic, weak vaccinia virus early/late promoter (elp4) and to remove 3'-non-coding sequences from the gpt gene cassette, the gpt open reading frame was amplified in a polymerase chain reaction (PCR) from pSV2gpt (ATCC #37145), using gpt gene specific oligonucleotides (5'-ATC ATA TGA GGA TCC ATG AGC GAA AAA TAC ATC GTC ACC-3' and 5'-ATC CCG GGA CGT CAT AAA AAG ATT AGC GAC CGG AGA TTG GCG G-3') that simultaneously introduced NdeI and BamHI sites at the 5'-end and AatII and SmaI sites at the 3'-end of the gpt gene. PCR products were cleaved with NdeI/SmaI and ligated with a NdeI/SmaI cut pFS51 vector (EP A 91 114 300.-6.). The elp4 sequence was introduced as a synthetic NdeI/BamHI linker, consisting of the annealed oligonucleotides oelP4.1, 5'-TAT GTA AAA GTT GAA ATT ATT TTT TTA TGC TGT AAA TAA GTT AAC A-3' and oelP4.2, 5'-GAT CTG TTA ACT TAT TTA CTA GCA TAA AAA AAT AAT TTC AAC TTT TAC A-3', upstream to the gpt open reading frame to obtain plasmid pelP4-gpt. The elp4-gpt gene cassette was cut out from plasmid pelP4-gpt with NdeI and AatII and ligated with NdeI/AatII cut and purified pselP-gpt-L2 vector DNA resulting in pselP-elp4gpt-L2.

pselP-elp4gpt-L2/T7. The 2.7 kB BamHI fragment with the gene of the bacteriophage T7 RNA polymerase was isolated from the vaccinia virus vTF7/3 (Fuerst et al., 1986) and ligated with the BamHI cleaved and dephosphorylated pselP-elp4gpt-L2 vector. A plasmid clone carrying the T7 RNA polymerase gene in the correct orientation relative to the selP promoter was isolated. This plasmid was named pselP-elp4gpt-L2/T7.

Figure 1:
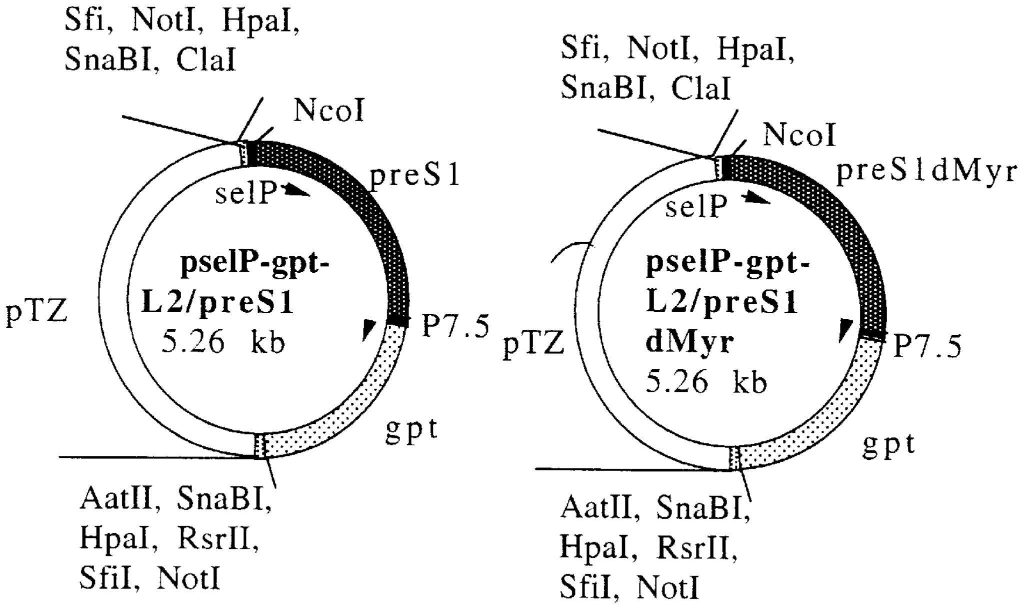
FIG. 1—Structure of the plasmids pselP-gpt-L2/preS1 and pselP-gpt-L2/preS1dMyr. The plasmid structure of the HBV large protein or HBV demyristylated large protein genes are given. Arrows indicate the direction of transcription from the selP and P7.5 promoters.

To construct an optimal transcription unit the 5'-non-coding sequences of the preS1-S2-S gene were completely removed. An NcoI site (5'-CCATGG-3') was introduced around the ATG start codon by site directed mutagenesis. This manipulation allowed the direct fusion of the ATG start codon of the respective genes with the vaccinia virus early/late promoter (selP) or the bacteriophage T7 promoter. The plasmids pselP-gpt-L2/preS1 and pselP-gpt-L2/preS1dMyr (FIG. 1) were constructed to introduce the preS1-S2-S-sAg gene or its demyristylated version, respectively, under the control of the selP promoter, together with the *E. coil* gpt marker gene under the control of the weak vaccinia promoter P7.5 into the genome of vaccinia virus. The double gene cassettes can be excised from the plasmids with several restriction enzymes (e.g., NotI, SnaBI, SfiI) and ligated into the respective unique sites of a suitable vaccinia virus vector. The cassettes were excised with NotI and ligated with NotI cleaved vaccinia vector arms. Since the Not cassette isolated from pselP-gpt-L2/preS1 or pselP-gpt-L2/preS1dMyr can ligate with the NotI-cleaved vector arms in two different orientations, a diagnostic restriction endonuclease digest was performed using the enzymes XbaI and SacI. The latter enzyme allowed in parallel the examination for the presence of vaccinia wild-type virus using SacI cleaved wild-type DNA as a reference. The strong early/late promoter has been described in U.S. Ser. No. 07/882,768.

In the plasmids pTZ-L2/preS1 and pTZ-L2/preS1dMyr (FIG. 8) the HBV large antigen gene or its demyristylated version were placed under the control of the bacteriophage T7 promoter. The viruses constructed with these plasmids were designated the vT7S1 series and the vT7S1dM series, respectively.

pTZ-L2/CRM228A. The nucleotide sequence coding for the A fragment of the Corynebacteriophage beta tox 228 polypeptide (without signal peptide sequence) is amplified in a polymerase chain reaction using the PCR primers 5° CCT TCA GCC CAT GCC ATG GCT GAT GAT GTT 3' and 5' A GCC ACC TAC TGC AGG CCT GAC ACG 3'. The upstream primer introduces an NcoI site while the downstream primer introduces a PstI site. The 606 bp PCR product is cleaved with NcoI and PstI and cloned into the NcoI/PstI cut pTZ-L2 vector (see U.S. Ser. No. 07/914,738), resulting in plasmid pTZ-L2/CRM228A.

pTZ-L2/preS1dMyr-CRM228A. An NcoI site is introduced at the C-terminus of the preS1dMyr open reading frame (ORF) using single-stranded DNA from pTZ-L2/preS1dMyr as a template and the mutagenic oligonucleotide 5' TTT TGT TAG GGT TTC CAT GGA TAC CCA AAG ACA 3'. This manipulation changes the last two amino acids of the preS1dMyr open reading frame from Tyr-Ile to Ser-Met and introduces an additional Glu residue. The resulting plasmid is designated pTZ-L2/preS1dMyrdTAA. This plasmid is linearized with PstI, partially digested with NcoI and ligated with the NcoI/PstI insert of plasmid pTZ-L2/CRM228A. A plasmid clone carrying the gene for the CRM228 A fragment is selected and designated pTZ-L2-preS1.

pTZ-L2/preS2-CRM228A. An NcoI site is introduced at the C-terminus of the preS2 open reading frame using single-stranded DNA from plasmid pTZ-L2/preS2 as a template and the mutagenic oligonucleotide 5' TTT TGT TAG GGT TTC CAT GGA TAC CCA AAG ACA 3'. This manipulation changes the last two amino acids of the preS2 ORF from Tyr-Ile to Ser-Met and introduces an additional Glu residue. The resulting plasmid is designated pTZ-L2/preS2dTAA. This plasmid is linearized with PstI, partially digested with NcoI and ligated with the NcoI/PstI insert of plasmid pTZ-L2/CRM228A. A plasmid clone carrying the gene for the CRM228 A fragment is selected and designated pTZ-L2/preS2-CRM228A.

pTZ-L2/sAg-CRM228A. An NcoI site is introduced at the C-terminus of the HBV sAg open reading frame using single-stranded DNA from plasmid pTZ-L2/sAg as a template and the mutagenic oligonucleotide 5' TTT TGT TAG GGT TTC CAT GGA TAC CCA AAG ACA 3'. This manipulation changes the amino acid sequence of the HBV sAg ORF from Tyr-Ile to Ser-Met and introduces an additional Glu residue. The resulting plasmid is designated pTZ-L2/sAgdTAA. This plasmid is linearized with PstI, partially digested with NcoI and ligated with the NcoI/PstI insert of plasmid pTZ-L2CRM228A. A plasmid clone carrying the gene for the CRM228 A fragment was selected and designated pTZ-L2/sAg-CRM228A.

pTZ-L2/preS1dMyr(×2). The nucleotide sequence comprising the amino acids 1–108 of the preS1dMyr ORF is amplified in a PCR reaction using pTZ-L2/preS1dMyr as a template and the oligonucleotides 5' TTT TGG AAT ATA AAT AAG GC 3' and 5' ATT CCA CTC CAT GGC CTG AG 3' as PCR primers, the latter of which introduces a second NcoI site into the PCR product. The 360 bp PCR product is cut with NcoI and ligated with NcoI-cut and calf intestinal phosphatase-treated pTZ-L2/preS1dMyr vector. A plasmid carrying the PCR product in the correct orientation relative to the preS1 ORF is selected and designated pTZ-L2/preS1dMyr(×2).

EXAMPLE 2

In vitro Cloning of Chimeric Vaccinia Viruses

The NotI gene cassettes from the preS1-, preS1dMyr- or T7 polymerase-containing plasmids (pTZ-L2/preS1, pTZ-L2/preS1dMyr, pselP-gpt-L2/preS1, pselP-gpt-L2/preS1dMyr, pselP-elp4gpt-L2/T7) were isolated and ligated with the NotI-cut genomic DNA from vaccinia virus wild-type strain WR, essentially as described in U.S. Pat. No. 5,445,953. The ligation reagents consisted of 1 Ag NotI cut vaccinia virus genomic DNA, 500 ng NotI cassette purified from the corresponding plasmids, 5 units of T4 DNA ligase and reaction buffer in a total volume of 50 $\mu$l. After incubation for 16 hours at 16° C., the ligation mixture was coprecipitated with calcium phosphate and added to subconfluent CV-1 cells. These cells had been infected with fowlpox virus strain HP1-441 (Mayr & Malicki, 1966) two hours before at a multiplicity of infection (moi; viruses per cell) of 0.1 plaque forming units (pfu) per cell. Five to seven days post-infection, the cell monolayer was completely infected with vaccinia virus. Cells were harvested and virus was released from the cell debris by extensive sonification.

Selection for chimeric vaccinia virus was performed by titrating the virus progeny in the presence of 25 $\mu$g/ml mycophenolic acid, 15 $\mu$g/ml hypoxanthine and 125 $\mu$g/ml xanthin. Viruses grown under these conditions were further plaque-purified and used for the production of "small" and "large" virus stocks. Small virus stocks isolated from single virus plaques were also grown under selective conditions. Infected cells from small stocks were divided into two cultures. One culture was used for the production of crude virus stocks. From the other, DNA was isolated, digested with various restriction endonucleases and transferred to nitrocellulose filters. These filters were hybridized with specific probes to verify the orientation of the NotI cassette in the genome of the chimeric vaccinia virus and to confirm absence of wild-type vaccinia virus.

Figure 2:
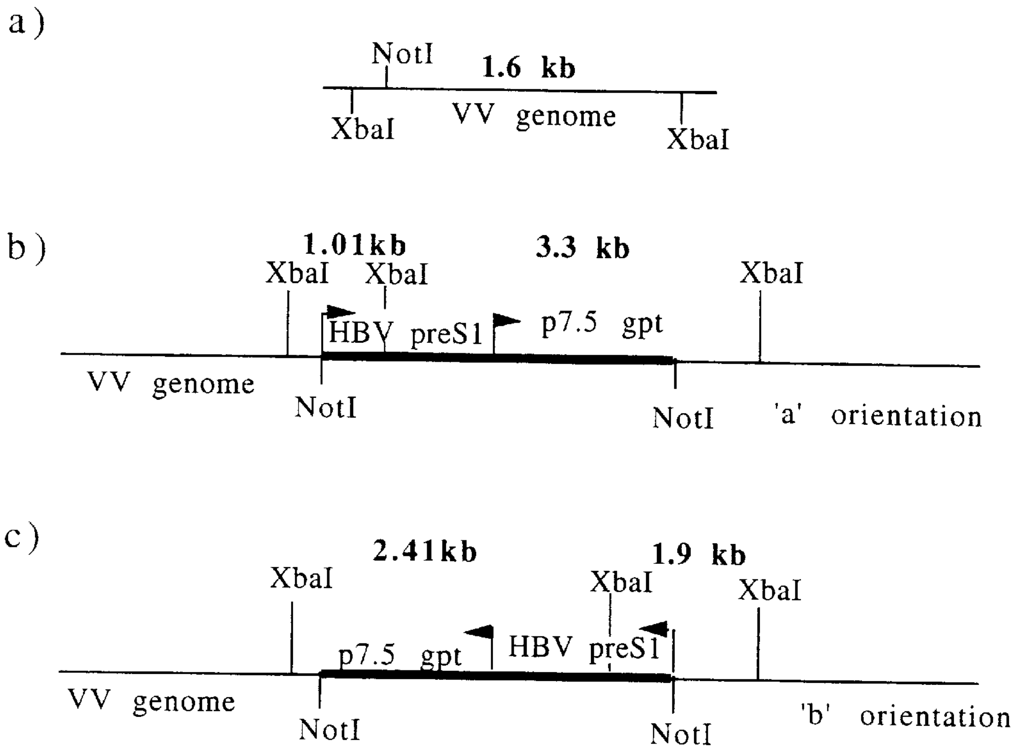
FIG. 2—XbaI restriction pattern of preS1 or preS1dMyr chimeric vaccinia viruses. The sizes of the XbaI fragments of the chimeric vaccinia viruses hybridizing to a $^{32}$P-labeled preS1-specific probe are shown. Arrows indicate the direction of transcription from the selP and P7.5 promoters.
Figure 3:
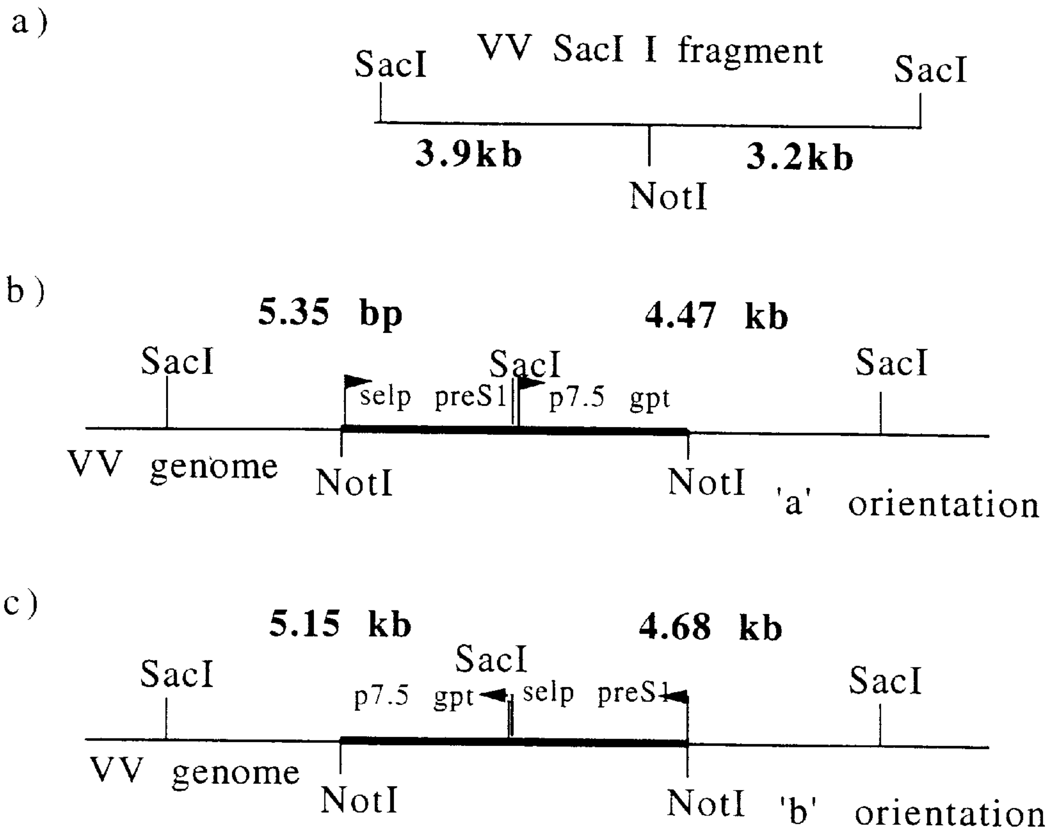
FIG. 3—SacI restriction pattern of preS1 or preS1dMyr chimeric vaccinia viruses. The figure shows the size of SacI fragments hybridizing to the $^{32}$P-labeled 7.1 kB vaccinia virus SacI "I" fragment of preS1 and preS1dMyr chimeric vaccinia viruses. Arrows indicate the transcription direction from the selP and P7.5 promoters.

The XbaI fragments from genomic DNA of a preS1 chimeric vaccinia virus hybridizing to a $^{32}$P-dCTP labeled preS1 specific probe should have a size of 1.01 kB and 3.3 kB or 1.9 kB and 2.41 kB depending on the orientation of the NotI cassette (FIG. 2) while the SacI fragments from the same chimeric virus, hybridizing to the $^{32}$P-dCTP labeled 7.1 kB vaccinia virus SacI "I" fragment should have a size of 5.35 kB and 4.47 kB or 5.15 kB and 4.68 kB depending on the orientation (FIG. 3). In FIG. 2*a,* the unique NotI site and the flanking XbaI sites in the wild-type vaccinia virus genome are shown. Integration of the NotI cassette into the unique NotI site in the "a" orientation results in the formation of two new XbaI fragments of 1.01 kB and 3.3 kB length (see FIG. 2*b*). Integration in the "b" orientation creates two new XbaI fragments of 2.41 kB and 1.9 kB length (see FIG. 2*c*). In FIG. 3*a,* the unique NotI site and the flanking SacI sites in the wild-type vaccinia virus genome are shown. Integration of the NotI cassette into the unique NotI site in the "a" orientation results in the formation of two new SacI fragments of 5.35 kB and 4.47 kB length (see FIG. 3*b*). Integration in the "b" orientation creates two new XbaI fragments of 5.15 kB and 4.68 kB length (see FIG. 3*c*). In case of contamination of chimeric virus stocks with wild-type vaccinia virus DNA, a 7.1 kB SacI fragment should also hybridize to the SacI "I" probe (FIG. 3*a*).

Figure 4:
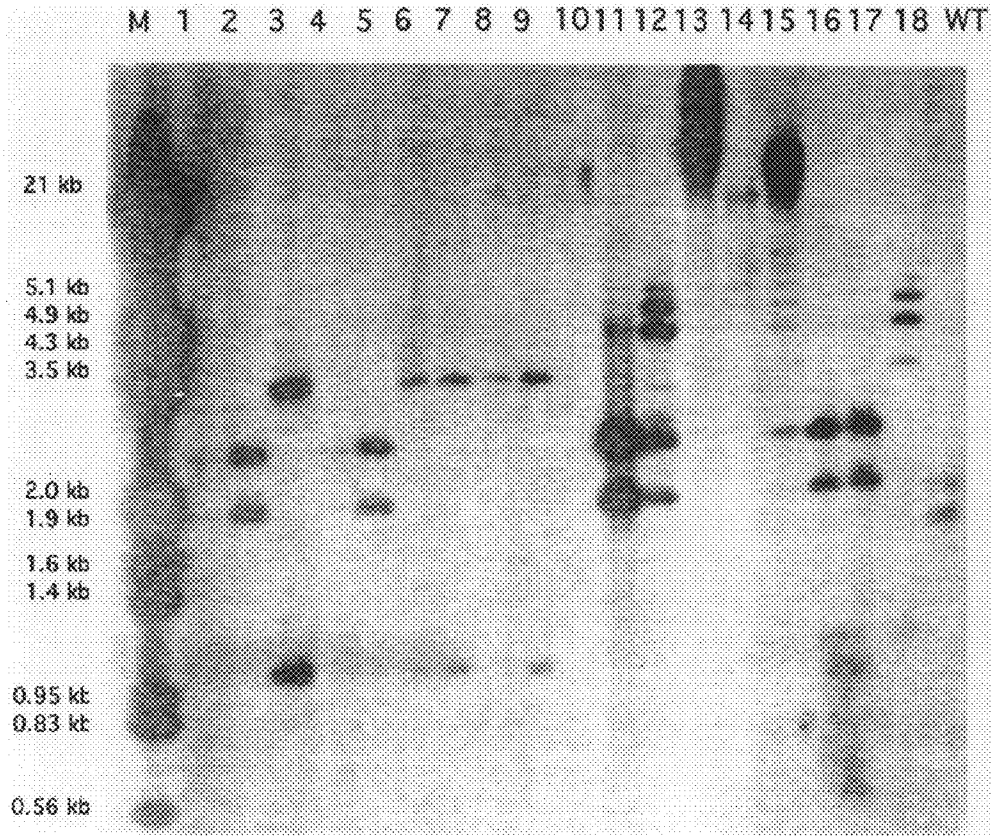
FIG. 4—Hybridization pattern to a $^{32}$P-labeled preS1-specific probe of XbaI-cleaved genomic DNA from CV-1 cells infected with preS1 or preS1dMyr chimeric vaccinia virus clones. CV-1 cells were infected with preS1 or preS1dMyr chimeric vaccinia virus clones or wild-type vaccinia virus. Lanes 1–10: XbaI-cleaved genomic DNA from CV-1 cells infected with vS1 #1–10. Lanes 11–18: XbaI-cleaved genomic DNA from CV-1 cells infected with vS1dM #1–6, 9 and 10. WT=XbaI-cleaved genomic DNA from CV-1 cells infected with wild-type vaccinia virus.
Figure 5:
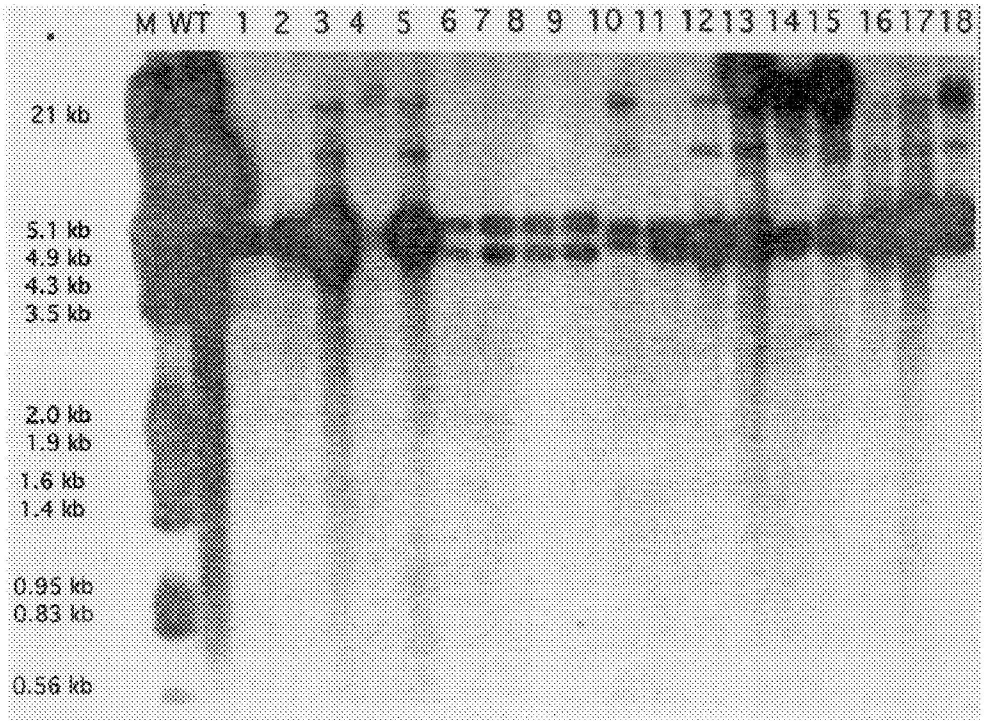
FIG. 5—Hybridization pattern to a $^{32}$P-labeled vaccinia virus SacI "I" fragment-specific probe of SacI-cleaved genomic DNA from CV-1 cells infected with vS1 or vS1dM chimeric viruses. CV-1 cells were infected with vS1, vS1dM or wild-type vaccinia virus. Lanes 1–10: SacI-cleaved genomic DNA from CV-1 cells infected with vS1 #1–10. Lanes 11–18: SacI-cleaved genomic DNA from CV-1 cells infected with vS1dM #1–6, 9 and 10. WT=SacI-cleaved genomic DNA from CV-1 cells infected with wild-type vaccinia virus.

The hybridization patterns of the XbaI and SacI cleaved genomic DNA from ten preS1 chimeric viruses, named vS1 #1–10, and 8 preS1dMyr chimeric viruses (named vS1dM #1–6, 9 and 10) with either the preS1 probe or the vaccinia virus SacI I probe are shown in FIGS. 4 and 5, respectively. In FIG. 4, genomic DNA was isolated from infected cell pellets and cleaved with XbaI. Fragments were separated on a 1% DNA agarose gel and transferred to nitrocellulose filters prior to hybridization to the probe. The hybridizing XbaI fragments indicated that vS1 #1, 2, 4 and 5 (FIG. 4, lanes 1, 2, 4 and 5) had the NotI cassette inserted in the 'b' orientation and the viruses vS1 #3, 6–9 (FIG. 4, lanes 3 and 6–9) in the 'a' orientation. The isolate vS1 #10 (lane 10) showed a weak hybridization signal in the high molecular weight range.

The viruses vS1dM #1, 2, 5, 6 and 9 (FIG. 4, lanes 11, 12, 15, 16 and 17) had their NotI cassette inserted in the 'b' orientation, the isolate vS1dM #10 (FIG. 4, lane 18) represents the 'a' orientation. Chimeric viruses vS1dM #3 and 4 (FIG. 4, lanes 13 and 14) had hybridization signals in a high molecular weight range. This type of signal also appeared in vS1dM #2 and 5 (FIG. 4, lanes 12 and 15) and in vS1dM #10 (FIG. 4, lane 18) and may indicate that multiple copies of the NotI cassette have been integrated into the viral genome. The precise structure of these viruses remains to be determined.

In FIG. 5, genomic DNA was isolated from infected cells and cleaved with SacI. Fragments were separated on a 1% DNA agarose gel and transferred to nitrocellulose prior to hybridization to the probe. Analysis of the SacI fragments hybridizing to the SacI I probe showed the expected patterns of the 'a' orientation (4.47 and 5.35 kB) and the 'b' orientation (4.68 kB and 5.15 kB). In addition, the 7.1 kB wild-type vaccinia virus SacI "I" fragment (FIG. 5, lane WT) is not present in any of the chimeric viruses. The possibility of contamination of chimeric viruses with wild-type vaccinia virus could therefore be excluded.

A chimeric vaccinia virus carrying the T7 RNA polymerase gene, vT7/selP, was constructed by integration of the NotI cassette from the plasmid pselP-elp4gpt-L2/T7 into the NotI site of vaccinia. This plasmid was constructed from the parental plasmid pselP-elp4gpt-L2 that harbors an improved gpt gene cassette. Starting from the vaccinia virus in vitro cloning plasmid pselP-gpt-L2 (U.S. Pat. No. 5,445,953) the plasmid pselP-elp4gpt-L2 was constructed as outlined in FIG. 7. In the prior vaccinia cloning plasmids carrying the gpt gene the dominant selection marker gene is controlled by the vaccinia P7.5 promoter present on a 500 base pair vaccinia DNA fragment. This fragment can give rise to unwanted recombination events with the two endogenous vaccinia genes coding for the 7.5 kDa polypeptide to which the P7.5 promoter segment is homologous. Venkatesan et al. (1981). To avoid this potential type of instability the P7.5-gpt gene cassette (1.1 kB in size) was replaced by the elp4-gpt-gene cassette (0.5 kB in size). The new gene cassette has, in addition to a weak, non-homologous synthetic early/late promoter, a substantially reduced size. The final plasmid containing the optimized dominant marker and the strong synthetic early/late promoter followed by a multiple cloning site was named pselP-elp4gpt-L2.

EXAMPLE 3

HBV Large Antigen Expression Experiments

The experiments were carried out with titrated crude stocks from chimeric vaccinia viruses. For this purpose, CV-1 cells (ATCC-CCL 70), SK-Hep1 cells (ATCC HTB 52) or Chang liver cells (ATCC CCL3), grown to confluency in 10 cm petri dishes ($5\times10^6$ cells) were infected at a moi of 1 with preS1 chimeric vaccinia viruses, preS1dMyr chimeric vaccinia viruses or chimeric vaccinia viruses with the preS1 or preS1dMyr genes under the control of the bacteriophage T7 promoter. Cells infected with the T7-preS1 chimeras were coinfected with a moi of 1 with a helper vaccinia virus chimera carrying the gene for the bacteriophage T7 RNA polymerase under the control of the selP promoter (vT7/selP). As a control, cells were infected with vT7/selP alone or were mock-infected. Cells were harvested three days post-infection. Infected cells were pelleted and resuspended in 300 $\mu$l sodium dodecyl sulphate (SDS) sample buffer. Ten to twenty $\mu$l of lysate were sonicated, boiled and electrophoresed on 12% SDS polyacrylamide gels.

Figure 6:
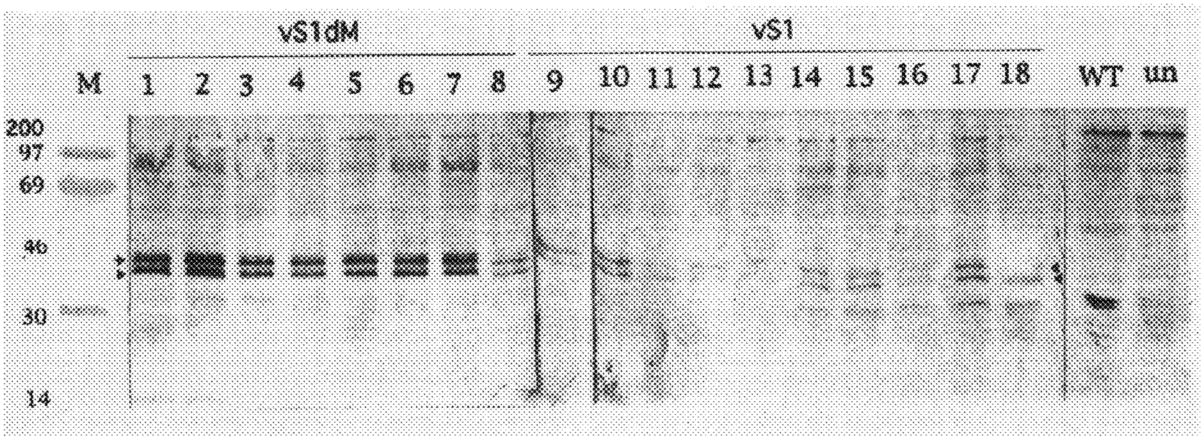
FIG. 6—Western blot analysis of total proteins of CV-1 cells infected with vS1 or vS1dM chimeric vaccinia viruses. Arrows indicate the two glycoforms of the HBV large protein with a molecular weight of 39 kDa or 42 kDa, respectively. Lanes 1–8: lysates from CV-1 cells infected with vS1dM #1–6, 9 and 10. Lanes 9–18: lysates from CV-1 cells infected with vS1 #1–10. WT=lysate from CV-1 cells infected with wild-type vaccinia virus; un=lysate from mock infected CV-1 cells; M=molecular weight standard in kilodaltons (kDa).

To evaluate the expression efficiency of the large antigen of all selected chimeras, lysates from infected CV-1 cells were analyzed in a Western Blot. FIG. 6 shows the expression levels in CV-1 cells infected with the eight vS1dM isolates (FIG. 6, lanes 1–8) or the 10 vS1 isolates (FIG. 6, lanes 9–18). Neither the orientation of the NotI gene cassettes nor the unexpected integration events seen in FIGS. 4 and 5 influence the expression efficiency of the vS1dM viruses (FIG. 6, lanes 1–8). The direct comparison of the expression levels of cells infected with the vS1dM viruses (FIG. 6, lanes 1–8) with the vS1 viruses (FIG. 6, lanes 9–18) indicates that the modification in the preS1 gene region, i.e., the deletion of the myristylation site, resulted in a significant increase of expression of the large antigen. Since total cellular proteins were analyzed in this experiment this effect is not due to a better solubility of the demyristylated large antigen but more likely to an improved translation of the preS1dMyr messenger RNA (mRNA), or, alternatively to improved post-translational processing and transport events. The molecular weights of the recombinant HBV large antigen corresponded to the ones synthesized in natural HBV infection. The two glycoforms with molecular weights of 39 kDa and 42 kDa, respectively, could clearly be distinguished.

For the expression studies with the vaccinia-T7 system, CV-1 cells were coinfected with the vT7S1 or the vT7S1dM viruses and with the second virus, vT7/selP, carrying the gene for the bacteriophage T7 RNA polymerase. Lysates from CV-1 cells infected with four different vT7S1dM isolates (FIG. 9, lanes 1–4) and 6 different vT7S1 viruses (FIG. 9, lanes 5–6 and 9–12) were analyzed. As a control, lysates from mock-infected or from CV-1 cells infected with vT7/selP were also analyzed (FIG. 9, lanes 7 and 8, respectively). The direct comparison of expression levels of the large antigen and its demyristylated version obtained in this system confirmed the results obtained with the conventional promoter constructs. CV-1 cells infected with the vT7S1dM viruses produce significantly more large protein than cells infected with the vT7S1 chimeras. A careful quantification indicated at least a five-fold higher production rate of the modified versus the wild-type large antigen.

EXAMPLE 4

Quantification of the Large Antigen by Western Blot Analysis

Expression levels were compared in a Western blot carried out essentially according to Towbin et al. (1979), with the following modifications. The first antibody was either an anti-human hepatitis associated antigen (HAA) serum developed in goat (Axell, Cat. No. AXL 683) or a preS1 region-specific mouse monoclonal antibody (Immunotech S.A. Cat. No. 0866) used in a 1:200 dilution in Western Blot buffer (phosphate buffered saline containing 0.1% Tween 20). The second antibody was an alkaline phosphatase coupled goat anti mouse serum (Sigma Chemicals, Inc. Cat. No. A-4656) in a 1:1000 dilution. The detection system (NBT and bovine calf intestinal phosphatase) was from Promega, Inc.

Quantification of the large HBV antigen was performed by scanning of the Western blot bands. As an internal standard purified HBV ayw middle antigen expressed in the Vero cell/vaccinia virus system was used. Serial dilutions were made from purified middle antigen and from large antigen preparations. Dilutions were electrophoresed on a 12% SDS polyacrylamide gel, transferred to nitrocellulose and analyzed in a Western blot using the anti-HAA serum as a first antibody and a alkaline phosphatase-conjugated anti-goat IgG serum as a second antibody. Depending on the cell type, the cell culture conditions and the viral vectors used 1–10 $\mu$g of large antigen/$10^6$ cells were detected.

In order to compare HBV large antigen expression levels CV-1 cells (a monkey kidney cell line), SK-Hep1 and Chang liver cells (both human liver cell lines) were infected with vS1 #9 ("a" orientation) and vS1 #10 ("b" orientation), or with vS1dM #9 ("b" orientation) and vS1dM #10 ("a" orientation, probably multiple inserts). In parallel, all cell lines were infected with wild-type vaccinia virus as a control. FIG. 10 shows the results of the expression study. Lysates from SK-Hep1 (S), Chang Liver (Ch) and CV-1 (C) cells infected with vS1 #9 and vS1 #10, wild-type vaccinia virus and vS1dM #9 and vS1dM #10 were compared. Again the increased expression levels of the chimeras with the demyristylated preS1 gene (FIG. 10, lanes 11–16) compared to those with the wild-type preS1 gene (lanes 1–6) was clearly visible. This result demonstrated that this effect was not restricted to a single cell line but could repeatedly be observed in different cell lines.

In addition, all cell lines express the authentic two molecular forms of the large antigen observed in FIG. 6. However, the expression levels differed significantly. Chang liver cells (FIG. 10, lanes 2, 5, 12 and 15) synthesize the large antigen much less efficient than SK-Hep1 cells (lanes 1, 4, 11 and 14) or CV-1 cells (lanes 3, 6, 13 and 16). This finding demonstrated the importance of selecting the optimal cell line.

The direct comparison of expression levels from the bacteriophage T7 promoter versus the vaccinia virus selP promoter was done in parallel. For this purpose lysates from CV-1 cells infected with the vT7S1 and vT7S1dM isolates were also analyzed in the Western Blot shown in FIG. 10. The difference in expression levels of the large antigen or its modified version was analyzed in a comparative Western blot. Expression levels of the large antigen or its modified version in the T7 system were at least five-fold higher as compared to the levels found in the selP promoter system (FIG. 10, lanes 6 versus 7, or 16 versus 17, respectively).

In order to compare precisely preS1 expression levels of the chimeric virus carrying the preS1 wild-type gene under the control of the vaccinia selP promoter (vS1#10, weakest preS1 expression; see FIG. 10, lane 3) with that of the chimeric virus carrying the modified preS1 gene under the control of bacteriophage T7 promoter (vT7S1dM, strongest preS1 expression; see FIG. 10, lane 17), dilutions of cell lysates from both infections were analyzed in a Western blot. To quantitate the obvious differences seen in FIG. 11, Panel A, blots were subjected to densitometric scanning.

Cultures of $1\times10^7$ CV-1 cells were infected with vLS1#10 at an moi of 2 pfu/cell or with vT7S1dM and the helper virus vT7/selP at an moi of 1 pfu/cell for each chimeric virus. Forty-eight hours post-infection, infected cells were harvested and resuspended in 1 ml of SDS sample buffer. Lysates were sonicated extensively and further diluted in SDS sample buffer. Twenty $\mu$l of diluted lysate was separated in a 12% SDS polyacrylamide gel. Gels were either used for transfer of proteins to a nitrocellulose filter (Western blot) or proteins were stained with Coomassie Blue. FIG. 11, Panel A shows immune stained filters. Indicated filters were analyzed with a densitometric scanner (Hirschmann Elscript 400). The Coomassie Blue stained 1:30 dilutions of lysates from each infection are shown in FIG. 11, Panel B. The result of the densitometric scanning analysis of the Western blot signals obtained from optimal dilutions (1:10 of lysate vS1#10 lysate; 1:50 of lysate vT7S1dM) are given in FIGS. 12A and 12B. The two peaks correspond to the two preS1 glycoforms. Regarding the different dilution factors (1:10 versus 1:50) and the peak areas of the scan (43,198 versus 104,659), it is clear that the expression of the modified preS1 gene from the bacteriophage T7 promoter is 12 times more efficient than expression of the wild-type preS1 gene controlled by the vaccinia selP promoter.

EXAMPLE 5

Enhancing Protein Immunogenicity: Construction of Hybrid Proteins Consisting of HBV Surface Glycoprotein and the Diphtheria Toxin A Fragment Cross-reacting Material and Duplication of HBV preS1-specific Epitopes In some cases, it may be desirable to enhance the immunogenicity of a Hepatitis B virus vaccine by coupling HBV preS1 peptides to powerful immune potentiators. In this example, a novel immune potentiator, diphtheria toxin cross-reacting material (CRM), is employed to enhance the immune response to HBV surface antigens. CRM's are nonfunctional forms of diphtheria toxin that cross react with diphtheria toxin antiserum. A strong immune response is induced by *Corynebacterium diphtheriae* expressing CRM. "Pharmacology of Bacterial Toxins," in *International Encyclopedia of Pharmacology and Therapeutics,* ed. Dorner and Drews, pp. 693–708 (1986). The diphtheria toxin gene or CRM gene is carried in a lysogenic β-phage which may or may not integrate into the bacterial genome. The intact toxin consists of an "A" fragment with a molecular weight of 22 kD and a "B" fragment with a molecular weight of 40 kD. The A fragment provides the toxic enzymatic whereas the B fragment is necessary for the transfer of the A fragment across the cell membrane. CRM 228 resembles the wild-type toxin but has no enzymatic activity due to changes in the amino acid sequence. Uchida et al., *J. Biol. Chem.* 248:3838–44 (1973a); Streeck et al., *Science* 221:855–58 (1983). The phage carrying the gene for CRM 228 is available from Institut Pasteur, Paris, France.

To improve the immunogenicity of the demyristylated large protein (preS1-S2-S-sAg) or of the two smaller HBV surface glycoproteins preS2-S-SAg and S-sAg, CRM 228 A is fused to these antigens. The linkage of the glycoprotein-encoding DNA with the nucleic acid encoding the CRM 228 A fragment is effected by recombinant DNA methods. See FIG. 13. Thus, the antigen and the immunopotentiator are joined genetically and expressed as fusion proteins. The A fragment has been selected because of its smaller size compared to the CRM 228 B fragment. The CRM 228 B fragment or the complete CRM 228 proteins exceed the size of the preS1-S2-S-sAg, which might have a negative effect on the immune response directed against the preS1 moiety. The smaller size of the CRM 228 A fragment is helpful in ensuring accessibility to the preS1 epitopes within the fusion protein. The strong immunogenicity of the A fragment, however, is equivalent to that of the native molecule.

An alternative method for joining HBV antigens and immunopotentiators is by the chemical linkage of highly purified CRM 228 A fragment with purified preS1-preS2-S-sAg (demyristylated version), preS2-S-sAg or S-sAg. For this purpose, equimolar amounts of the CRM 228 A fragment and the antigen to be joined are cross-linked using standard chemical procedures. For example, Widder and Green, *Methods in Enzymology* 112:207 (1985).

Another method for increasing the immunogenicity of preS1-containing antigens is to duplicate the preS1 region of HBV large antigen (amino acids 1–108). This is effected inserting a second copy of the preS1-coding region into a vector coding for the entire HBV large antigen. See FIG. 14. Expression of this construct gives the new protein $(preS1)_2$-preS2-S-sAg which contains two preS1 B- and T-cell specific epitopes.

EXAMPLE 6

Vaccines

In another embodiment, the proteinaceous particles of the present invention are used in a pharmaceutically-acceptable composition that, when administered in an effective amount, is capable of inducing protective immunity against HBV infection.

The preparation of vaccines which contain proteins as active ingredients is well understood in the art. Typically, such vaccines are prepared as injectables, either as liquid solutions or suspensions; solid forms suitable for solution in, or suspension in, liquid prior to injection may also be prepared. The preparation may also be emulsified. The active immunogenic ingredient is often mixed with an excipient which is pharmaceutically-acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH-buffering agents, adjuvants or immunopotentiators which enhance the effectiveness of the vaccine.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glucose or triglycerides; suppositories may be formed for mixtures containing the active ingredient in the range of 0.5% to 10%, preferably 1.2%. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders and contain 10%–95% of active ingredient, preferably 25–70%.

The proteinaceous particles can be formulated into the vaccine as neutral or salt forms. Pharmaceutically acceptable salts, include acid addition salts (formed with the free amino groups of the peptide) and inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The term "unit dose" refers to physically discrete units suitable for use in humans, each unit containing a predetermined-quantity of active material calculated to produce the desired therapeutic effect in association with the required diluent; i.e., carrier, or vehicle and a particular treatment regimen. The quantity to be administered, both according to number of treatments and amount, depends on the subject to be treated, capacity of the subject's immune system to synthesize antibodies, and degree of protection desired. Precise amounts of active ingredient required to be administered depend on the judgment of the practitioner and are peculiar to each individual. However, suitable dosage ranges are of the order of one to several hundred micrograms active ingredient per individual. Suitable regimes for initial administration and booster shots also vary, but are typified by an initial administration followed in one or two week intervals by one or more subsequent injections or other administration.

EXAMPLE 7

Production of Monoclonal Antibodies Specific for HBV ayw preS1

Three month-old female BALB/c mice were inoculated five times with purified HBV ayw preS1 expressed in Vero cells infected with the appropriate vaccinia virus chimera (approximately 1–10 $\mu$g protein per inoculation) by a variety of routes over a six week period. Three days after the final inoculation, blood samples were taken from immunized mice and assayed for preS specific antibodies using an ELISA system with preS1 as a capture antigen. Spleen cells from mice with a positive ELISA signal were isolated and fused with the plasmacytoma cell line P3X63Ag8 (ATCC TIB 9) by using polyethylene glycol according to the method of Lane et al., *J. Immunol. Meth.* 81:223–228 (1985). Hybridoma cell clones secreting preS specific monoclonal antibodies were selected in a limited dilution assay in RPMI 1640 medium (8041-2400, GIBCO). The specificity for the preS1 portion of the monoclonal antibodies was verified with synthetic preS1 peptides in a commercially available peptide mapping kit (Cambridge Research Biochemicals).

EXAMPLE 8

Diagnostic Systems

A diagnostic system, preferably in kit form, useful for detecting the presence of preS1-containing antigens or antibodies to preS1-containing antigens in a body sample, includes (a) a protein of the present invention or (b) antibody of the present invention and (c) a labeled specific binding agent for signaling the presence of the immunoreaction of a preS1-containing protein and an anti-preS1 antibody.

As used herein, the term "label" in its various grammatical forms refers to single atoms and molecules that are either directly or indirectly involved in the production of a detectable signal to indicate the presence of a immunoreactant. Any labeling means can be linked to or incorporated in a specific binding agent or used separately, and those atoms or molecules can be used alone or in conjunction with additional reagents. Such labels are themselves well-known in immunochemistry and constitute a part of this invention only insofar as they are utilized with otherwise novel proteins methods and/or systems.

The diagnostic kits of the present invention are typically used in an "ELISA" format to detect the presence or quantity of anti-preS1 antibodies or preS1-containing proteins in a body sample such as serum or plasma. "ELISA" refers to an enzyme-linked immunosorbent assay that employs an antibody or antigen bound to a solid phase and an enzyme-antigen or enzyme-antibody conjugate to detect and quantify the amount of antigen or antibody present in a sample. A description of the ELISA technique is found in Chapter 22 of the 4th Edition of *Basic and Clinical Immunology* by D. P. Sites et al., Lange Medical Publications, Los Altos, Calif. (1982) and U.S. Pat. Nos. 3,654,090, 3,850,752, and 4,016,043, which are all incorporated by reference herein.

In preferred embodiments, the preS1-containing protein of the present invention or the anti-preS1 antibody of the present invention is affixed to a solid matrix to form a solid support. The molecules are typically affixed to the solid matrix by adsorption from an aqueous medium, although several other modes of adsorption, as well as other modes of affixation, well known to those skilled in the art can be used. Exemplary of such modes are the interaction of proteins with the carboxyl entity produced by the reaction of cyanogen bromide with glucose-containing matrices. These matrices include cross-linked dextrose or cellulose and glutaraldehyde linking, as discussed below in conjunction with latex particles and the like.

Useful solid matrices are well known in the art. Such materials include the cross-linked dextran available under the trademark SEPHADEX from Pharmacia Fine Chemicals (Piscataway, N.J.), agarose, beads of polystyrene from about 1 $\mu$m to about 5 mm in diameter (Abbott Laboratories of North Chicago, Ill.), polyvinyl chloride, polystyrene, cross-linked polyacrylamide, nitrocellulose of nylon-based webs such as sheets, strips, paddles, tubes. A preferred matrix is in the form of a plate or the well of a microtiter plate such as those made from polystyrene or polyvinylchloride. A microtiter plate and one or more buffers can also be included as elements of the diagnostic kit.

We claim:

1. A method for high yield production of hepatitis B virus preS1-preS2-S large antigen comprising the steps of (a) infecting a mammalian kidney cell with
  a chimeric vaccinia virus which comprises a synthetic vaccinia early/late promoter or a bacteriophage T7 promoter operatively linked to a polynucleotide that encodes the complete preS1-preS2-S hepatitis B virus large antigen;

(b) culturing the infected cell;

(c) lysing the infected cell; and (d) harvesting said antigen, wherein at least 1 $\mu$g of hepatitis B virus preS1-preS2-S large antigen is produced per $10^6$ cells.

2. A method for producing a proteinaceous particle consisting essentially of hepatitis B virus preS1-preS2-S large antigen, comprising the steps of:

(a) infecting a mammalian kidney cell with a chimeric vaccinia virus that comprises a synthetic vaccinia early/late promoter or a bacteriophage T7 promoter, wherein the promoter is operatively linked to a polynucleotide that encodes a hepatitis B virus preS1-preS2-S large antigen;

(b) culturing the infected cell under conditions that allow the expression of the recombinant protein, wherein at least 1 $\mu$g of hepatitis B virus large antigen per $10^6$ cells per 24 hours is produced; and (c) harvesting said proteinaceous particle consisting essentially of hepatitis B virus pres1-pres2-S large antigen.

3. The method according to claim 2, wherein the promoter is a bacteriophage T7 promoter, and the mammalian kidney cell is coinfected with a second chimeric vaccinia virus comprising a polynucleotide encoding a bacteriophage T7 polymerase.

4. The method according to claim 2, wherein the mammalian kidney cell is a VERO cell or a CV-1 cell.

5. The method according to claim 2, further comprising the step of purifying the proteinaceous particle consisting essentially of hepatitis B virus preS1-preS2-S large antigen.

6. A method for high yield production of modified hepatitis B virus preS1-preS2S large antigen comprising:

(a) infecting a mammalian kidney cell with a chimeric vaccinia virus which comprises a synthetic vaccinia early/late promoter or a bacteriophage T7 promoter operatively linked to a polynucleotide that encodes the complete preS1-preS2-S large antigen, wherein the preS1-preS2-S large antigen lacks the myristylation site within the preS1 region;

(b) culturing the infected cell;

(c) lysing the infected cell; and (d) harvesting said antigen;

wherein at least a 5-fold increase in the production rate of the modified as compared to the wild-type hepatitis B virus large antigen is obtained.

7. The method according to claim 6, wherein at least 5 $\mu$g of hepatitis B virus large antigen is produced per $10^6$ cells.

8. The method according to claim 6, wherein the polynucleotide encoding the preS1-preS2-S large antigen has a G to C transversion at the fifth nucleotide of the preS1 coding region of the polynucleotide.

9. The method according to claim 6, wherein the promoter is a bacteriophage T7 promoter, and the mammalian kidney cell is coinfected with a second chimeric vaccinia virus comprising a polynucleotide encoding a bacteriophage T7 polymerase.

10. The method according to claim 6, wherein the mammalian kidney cell is a VERO cell or a CV-1 cell.

11. A method for producing a proteinaceous particle consisting essentially of modified hepatitis B virus preS1-preS2-S large antigen, wherein the method comprises:

(a) infecting a mammalian kidney cell with a chimeric vaccinia virus that comprises a synthetic vaccinia early/late promoter or a bacteriophage T7 promoter, wherein the promoter is operatively linked to a polynucleotide that encodes a hepatitis B virus preS1-preS2-S large antigen, wherein the preS1-preS2-S large antigen lacks the myristylation site within the preS1 region;

(b) culturing the infected cell under conditions that allow the expression of the recombinant protein, wherein at least a 5-fold increase in the production rate of the modified as compared to the wild-type hepatitis B virus large antigen is obtained; and (c) harvesting the particles produced, wherein said proteinaceous particles consist essentially of hepatitis B virus preS1-preS2-S large antigen that lacks the myristylation site within the preS1 region.

12. The method according to claim 11, wherein the polynucleotide encoding the preS1-preS2-S large antigen has a G to C transversion at the fifth nucleotide of the preS1 coding region of the polynucleotide.

13. The method according to claim 11, wherein the promoter is a bacteriophage T7 promoter, and the mammalian kidney cell is coinfected with a second chimeric vaccinia virus comprising a polynucleotide encoding a bacteriophage T7 polymerase.

14. The method according to claim 11, wherein the mammalian kidney cell is a VERO cell or a CV-1 cell.

15. The method according to claim 11, further comprising the step of purifying the proteinaceous particle consisting essentially of hepatitis B virus preS1-preS2-S large antigen that lacks the myristylation site within the preS1 region.

16. The method according to claim 11, wherein at least 5 $\mu$g of hepatitis B virus large antigen is produced per $10^6$ cells.

17. A method for producing a composition comprising proteinaceous particles consisting essentially of hepatitis B virus preS1-preS2-S large antigen p39 and gp42, wherein the method comprises:

(a) infecting a mammalian kidney cell with a chimeric vaccinia virus that comprises a synthetic vaccinia early/late promoter or a bacteriophage T7 promoter, wherein the promoter is operatively linked to a polynucleotide that encodes a hepatitis B virus preS1-preS2-S large antigen;

(b) culturing the infected cell under conditions that allow the expression of the recombinant protein, wherein about 1 $\mu$g of protein per $10^6$ cells per 24 hours are obtained; and (c) harvesting said particles produced, wherein said proteinaceous particles consist essentially of hepatitis B virus preS1-preS2-S large antigen p39 and gp42.

18. A method for producing a composition comprising proteinaceous particles consisting essentially of modified hepatitis B virus preS1-preS2-S large antigen p39 and gp42, wherein the method comprises:

(a) infecting a mammalian kidney cell with a chimeric vaccinia virus that comprises a synthetic vaccinia early/late promoter or a bacteriophage T7 promoter, wherein the promoter is operatively linked to a polynucleotide that encodes a hepatitis B virus preS1preS2-S large antigen, wherein the preS1-preS2-S large antigen lacks the myristylation site within the preS1 region;

(b) culturing the infected cell under conditions that allow the expression of the recombinant protein, wherein at least a 5-fold increase in the production rate of the modified as compared to the wild-type hepatitis B virus large antigen is obtained; and (c) harvesting said particles produced, wherein said proteinaceous particle consists essentially of hepatitis B virus preS1-preS2-S large antigen p39 and gp42 that lacks the myristylation site within the preS1 region.

* * * * *